United States Patent
Taniguchi et al.

(10) Patent No.: US 6,949,068 B2
(45) Date of Patent: Sep. 27, 2005

(54) ENDOSCOPE SHAPE DETECTOR

(75) Inventors: Akira Taniguchi, Hachioji (JP); Fumiyuki Onoda, Tama (JP); Jun Hasegawa, Hino (JP); Yoshitaka Miyoshi, Hachioji (JP); Shoichi Amano, Hino (JP); Chieko Aizawa, Hachioji (JP)

(73) Assignee: Olympus Corporation (JP)

( * ) Notice: Subject to any disclaimer, the term of this patent is extended or adjusted under 35 U.S.C. 154(b) by 358 days.

(21) Appl. No.: 10/137,932

(22) Filed: May 2, 2002

(65) Prior Publication Data

US 2002/0169361 A1 Nov. 14, 2002

(30) Foreign Application Priority Data

May 7, 2001 (JP) ........................................ 2001-136532

(51) Int. Cl.[7] .................................................. A61B 1/00
(52) U.S. Cl. ...................................... 600/117; 600/424
(58) Field of Search .............................. 600/101, 117, 600/118, 424

(56) References Cited

U.S. PATENT DOCUMENTS

| | | | | |
|---|---|---|---|---|
| 5,561,290 A | * | 10/1996 | Strobel et al. ........... | 250/252.1 |
| 5,840,024 A | * | 11/1998 | Taniguchi et al. ........... | 600/424 |
| 6,059,718 A | * | 5/2000 | Taniguchi et al. ........... | 600/117 |
| 6,432,041 B1 | * | 8/2002 | Taniguchi et al. ........... | 600/118 |
| 2004/0116775 A1 | * | 6/2004 | Taniguchi et al. ........... | 600/117 |

FOREIGN PATENT DOCUMENTS

| | | |
|---|---|---|
| JP | 08 107875 | 4/1996 |
| JP | 2001 046318 | 2/2001 |
| JP | 2001 046319 | 2/2001 |
| JP | 2002 85338 | 3/2002 |

* cited by examiner

*Primary Examiner*—John P. Leubecker
(74) *Attorney, Agent, or Firm*—Ostrolenk, Faber, Gerb & Soffen, LLP

(57) ABSTRACT

By disposing a plurality of magnetic-field generating elements in the inserted portion of an endoscope, and by detecting it using a magnetic-field detecting unit disposed around the inserted portion, the shape of the inserted portion inserted into a body cavity is detected and it is displayed on a display device. For this purpose, it is determined whether the inserted portion is in an effective detection range in which the insertion portion shape can be detected by a detecting unit with a practicable accuracy, and by changing the display color of the inserted portion shape based on the determination result, it can be easily checked whether the inserted portion is in the effective detection range.

19 Claims, 24 Drawing Sheets

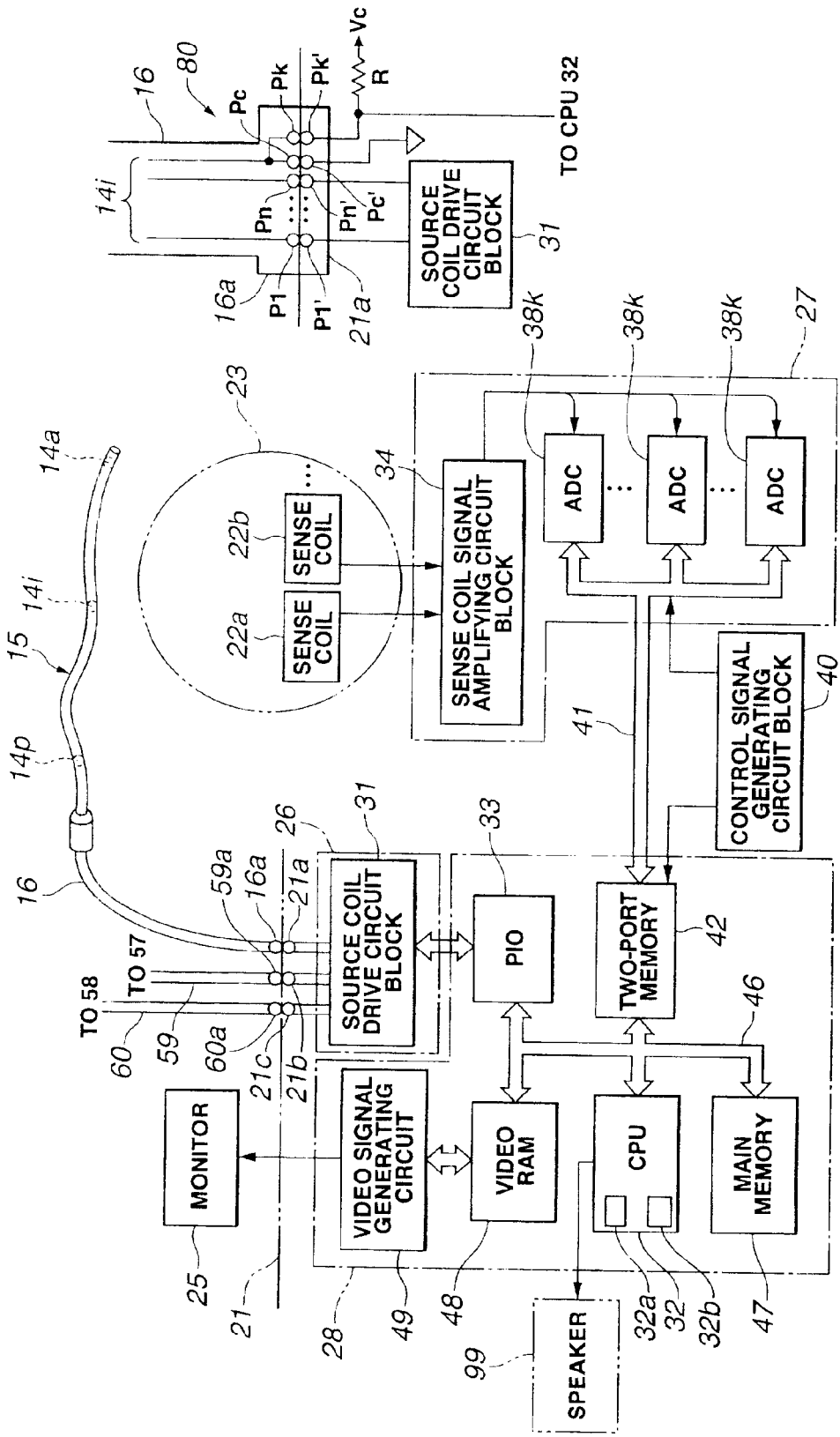

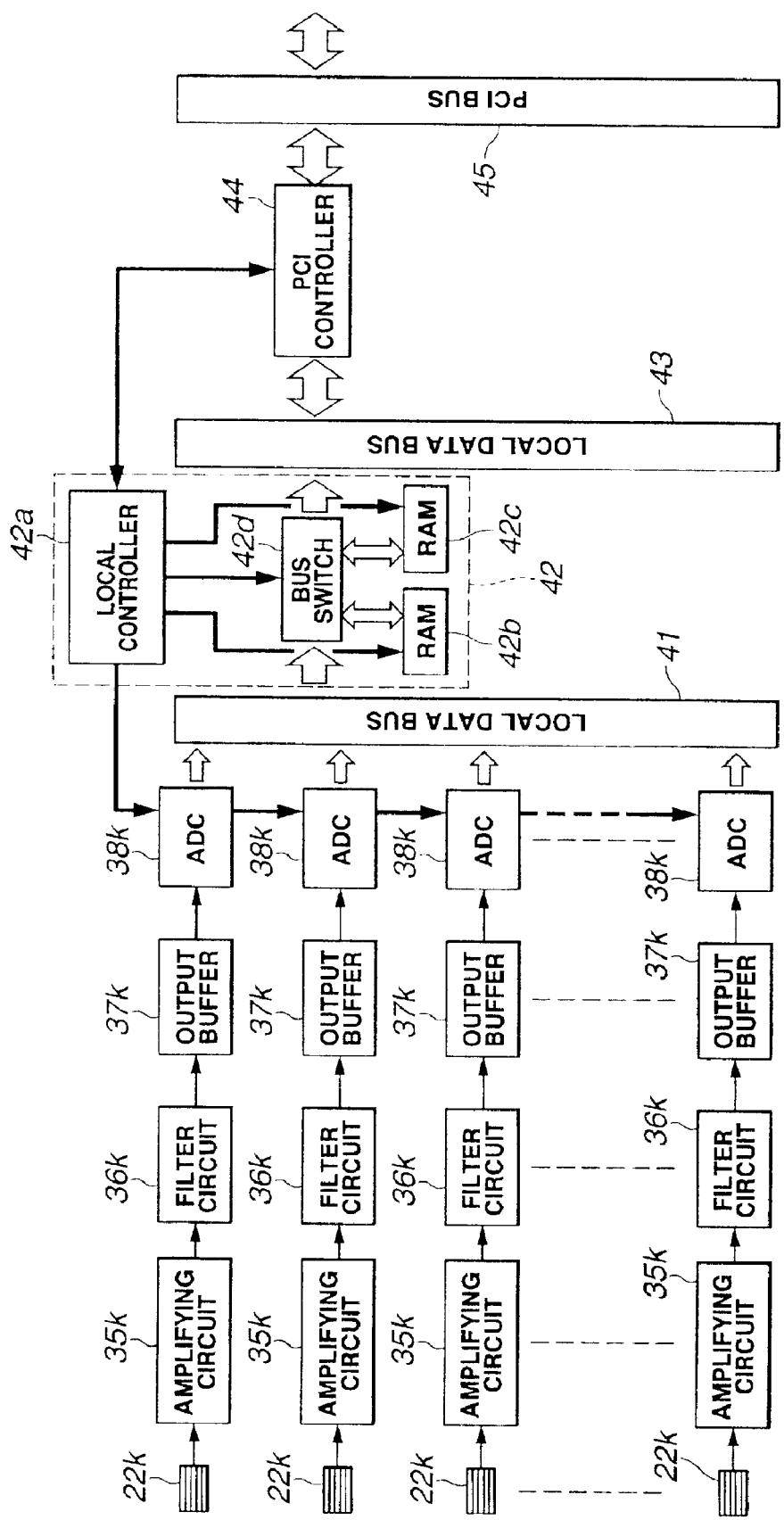

FIG.10

| SET MENUS AND ICONS | SET CONTENTS AND ICONS | | REMARKS |
|---|---|---|---|
| DISPLAY MODE CHANGEOVER | MODE OF DISPLAY FROM ABOVE | | DISPLAY MODE IS CHANGED OVER. |
| | MODE OF DISPLAY FROM BELOW | | |
| DATE AND TIME SETTING | DISPLAY FORM / DATE / TIME | | DATE AND TIME ARE SET. |
| THICKNESS ADJUSTMENT OF SCOPE MODEL | INDEX  THIN ◄────► THICK | | THICKNESS OF SCOPE MODEL IS ADJUSTED. THICKNESS OF SCOPE MODEL IS REPRESENTED BY POSITION INDEX. |
| PERSPECTIVE CHANGEOVER | WITH PERSPECTIVE | | PRESENCE/ABSENCE OF PERSPECTIVE OF SCOPE MODEL IS SET. |
| | WITHOUT PERSPECTIVE | | |
| BACKGROUND CHANGEOVER | SINGLE COLOR OF BLUE-GREEN | | BACKGROUND COLOR IS SET. |
| | BLUE-PURPLE GRADATION | | |
| DISPLAY CHANGEOVER | WITH INFORMATION DISPLAY | | PRESENCE/ABSENCE OF INFORMATION DISPLAY IS SET. |
| | WITHOUT INFORMATION DISPLAY | | |
| REGISTRATION OF SCREEN SETTING, AND CALL | ABOVE-DESCRIBED SETTING, AND MAGNIFICATION RATIO AND ROTATION AMOUNT OF SCOPE MODEL REGISTERED AND CALLED TO SUIT USER'S PREFERENCES. | | |

FIG.11A
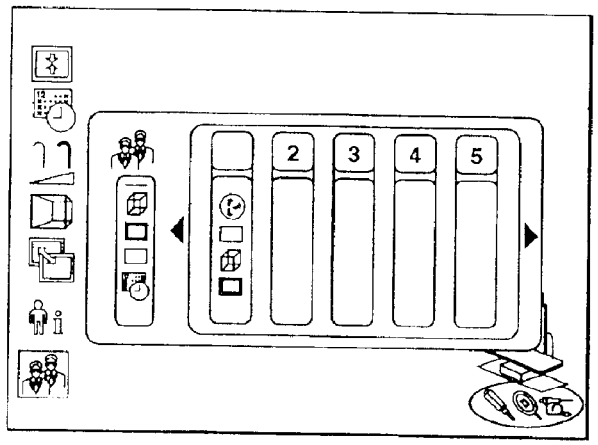
FIG.11B
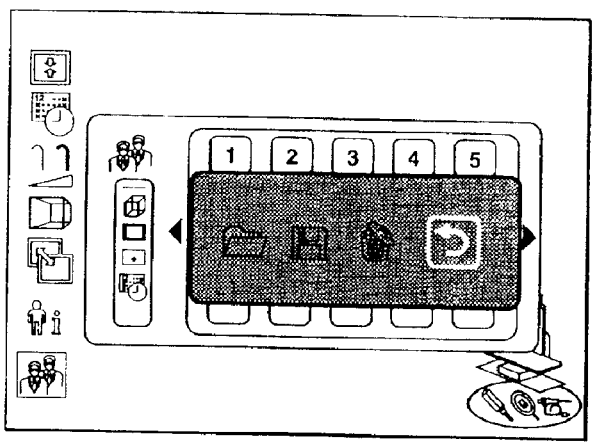
FIG.11C
| ICONS | DESIGNATIONS | FUNCTIONS |
|---|---|---|
| 📁 | CALL ICON | "SETTING" IS CALLED. |
| 💾 | REGISTER ICON | "SETTING" IS REGISTERED. |
| 🗑 | DELETE ICON | "SETTING" IS DELETED. |
| ↶ | CANCEL ICON | "SETTING" IS CANCELLED. |

25a

| ITEMS | DISPLAYS | CONTENTS |
|---|---|---|
| FORMS OF CONNECTION STATE DISPLAY | | DISPLAYED WHEN EXTRA CORPOREAL MARKER IS CONNECTED. |
| | | DISPLAYED WHEN REFERENCE PLATE IS CONNECTED. |
| | | DISPLAYED WHEN ENDOSCOPE IS CONNECTED. |
| COLORS OF CONNECTION STATE DISPLAY | GREEN COLOR | NORMAL |
| | YELLOW COLOR | OUTSIDE EFFECTIVE DETECTION RANGE |
| | RED COLOR | ABNORMAL OR OUT-OF ORDER |

FIG.15
| OPERATION NOTICE SYMBOLS | FUNCTIONS | |
|---|---|---|
| 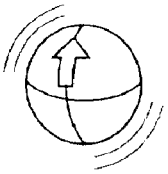 | ANGLE-UPWARD ROTATION 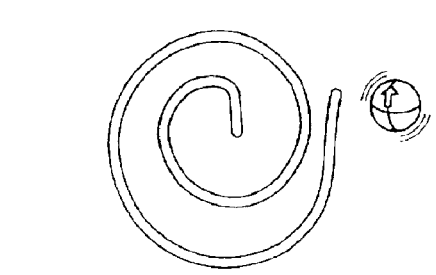 | |
| 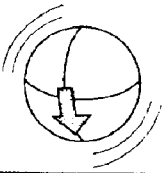 | ANGLE-DOWNWARD ROTATION | |
| 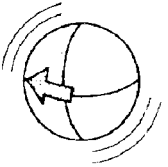 | ANGLE-LEFTWARD ROTATION | |
| 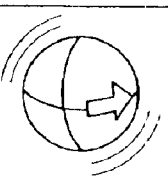 | ANGLE-RIGHTWARD ROTATION | |
| 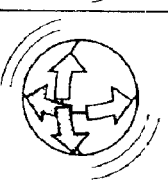 | VIEW RESET | |
| 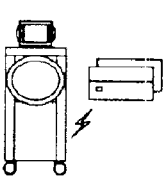 | VCV/DF INTERCOMMUNICATION STATE IN EVIS SYSTEM 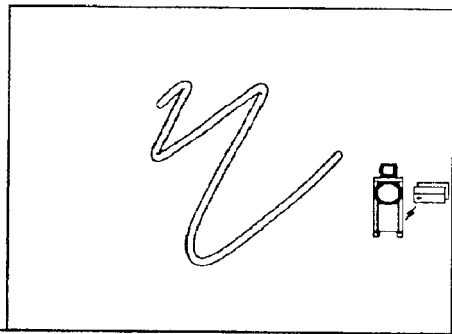 | BECAUSE SCREEN RENEWAL SPEED IS REDUCED DURING COMMUNICATION, NOTICE TO USER IS USING SYMBOLS. |

FIG.17

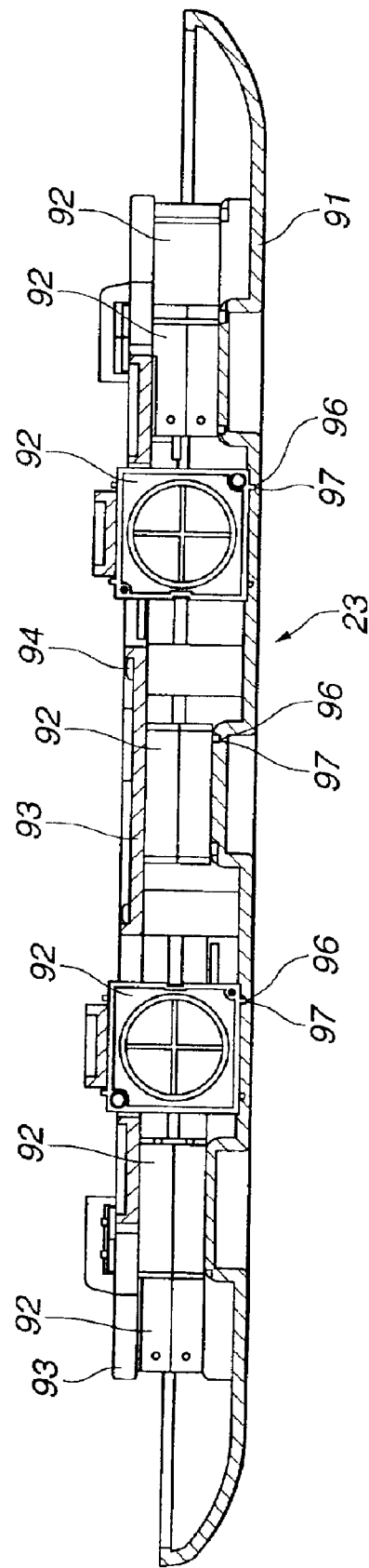

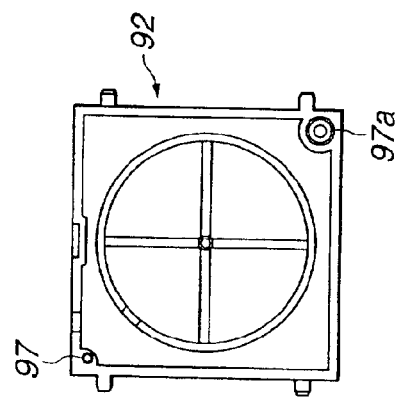
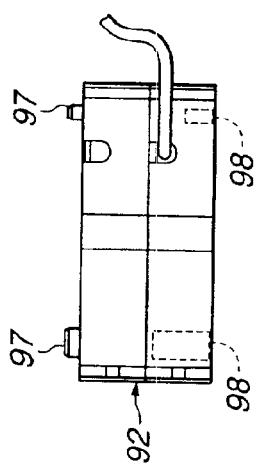
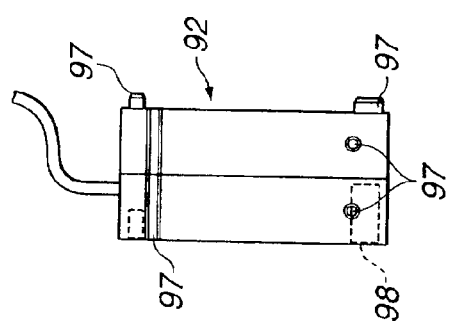
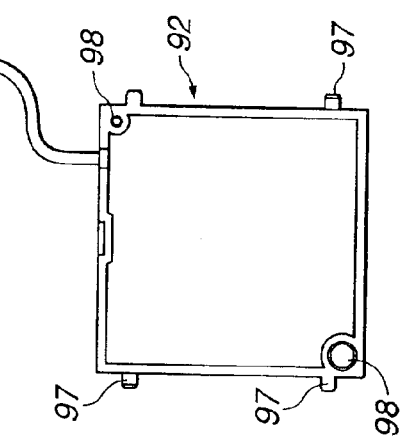
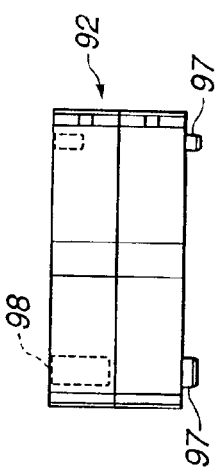
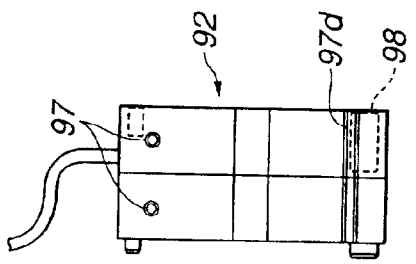

ENDOSCOPE SHAPE DETECTOR

This application claims benefit of Japanese Application No. 2001-136532 filed on May 7, 2001, the contents of which are incorporated by this reference.

BACKGROUND OF THE INVENTION

1. Field of the Invention

The present invention relates to an endoscope shape detector that detects the insertion shape of the endoscope and others using magnetic-field generating elements and magnetic-field detecting elements, and that displays them.

2. Description of the Related Art

In recent years, endoscope shape detectors have been used that detect the insertion shape of the endoscope inserted in a body cavity using magnetic-field generating elements and magnetic-field detecting elements, and that displays it by display means.

For example, Japanese Unexamined Patent Application Publication No. 8-107875 discloses an apparatus that detects the shape of the endoscope using magnetic fields, and displays the detected endoscope shape.

However, the detection range of magnetic-field detecting elements is finite because of the outputs of magnetic generating elements and sensitivities of magnetic detecting elements, and therefore, if the magnetic generating elements are located at positions at least a definite distance away from the magnetic detecting elements, a practicable detection accuracy cannot be obtained.

For example, in the arrangement disclosed in the Japanese Unexamined Patent Application Publication No. 8-107875, if the inserted portion of the endoscope of which the shape is to be detected moves to a position away from the magnetic detecting elements, a problem occurs that the actual shape of the inserted portion differs from the displayed shape.

SUMMARY OF THE INVENTION

Accordingly, it is an object of the present invention to provide an endoscope shape detector by which an operator can easily check whether the endoscope has fallen out of the detectable range in which the shape thereof can be detected with a definite accuracy.

It is another object to provide an endoscope shape detector by which insertion operation can be easily determined.

In order to achieve the above-described objects, the present invention provides an endoscope shape detector for detecting an endoscope shape that comprises a device to be detected, the device being disposed in an endoscope inserted portion inserted into a subject, or in other equipment; a detecting unit that detects the position of the device to be detected; a display device for displaying the insertion shape of the endoscope inserted portion, or the position of the other equipment, on the basis of the position information of the detecting unit detected by the detecting unit; a determining device that determines whether the device to be detected is in an effective detection range of the detecting unit, on the basis of the output of the detecting unit; and a display form selecting device that selects a display form by the display device, in the insertion shape display of the endoscope inserted portion or the display form by the display device, in the position display of the other equipment, on the basis of the determination result of the determining device. By the display form displayed by the display device, the operator can easily check whether the device to be detected has fallen out of the detectable range.

The above and other objects, features, and advantages of the present invention will be clear from the following detailed description of the preferred embodiments of the invention in conjunction with the accompanying drawings.

BRIEF DESCRIPTION OF THE DRAWINGS

FIGS. 1 to 25F are representations of an embodiment of the preset invention, and FIG. 1 is a block diagram showing the configuration of an endoscope system according to the embodiment;

FIG. 2 is a view showing an example of a coil arrangement incorporated in a coil unit according to the embodiment, the coil arrangement being represented by a standard coordinate system;

FIG. 3 is a block diagram showing the configuration of the endoscope shape detector in FIG. 1;

FIG. 4A is a block diagram showing the configurations of the detection block and the host processor in FIG. 3, and FIG. 4B is a view showing the configuration of a connection detecting mechanism;

FIG. 5 is a block diagram showing the configurations of the detection block, etc.;

FIG. 6 is a timing view showing the operation of a two-port memory, etc.;

FIG. 8 is a flowchart showing the main operation by the operation panel;

FIG. 10 is a view showing icons of a main menu bar and the functions thereof;

FIGS. 11A to 11C are views explaining the case where a set content such as the rotation of a scope model is registered;

FIG. 15 a view showing display functions by a view angle/select button;

FIG. 16 is a view showing functions of enlargement and others by a zoom button.

FIG. 17 is a view showing functions such as bipartition;

FIG. 23 is a sectional view showing a coil case having sense coils fitted thereto;

FIGS. 25A to 25F are views showing projections provided on each surface of the sense coils.

DESCRIPTION OF THE PREFERRED EMBODIMENTS

Hereinafter, an embodiment of the present invention will be described with reference to FIGS. 1 to 25F.

Figure 1:
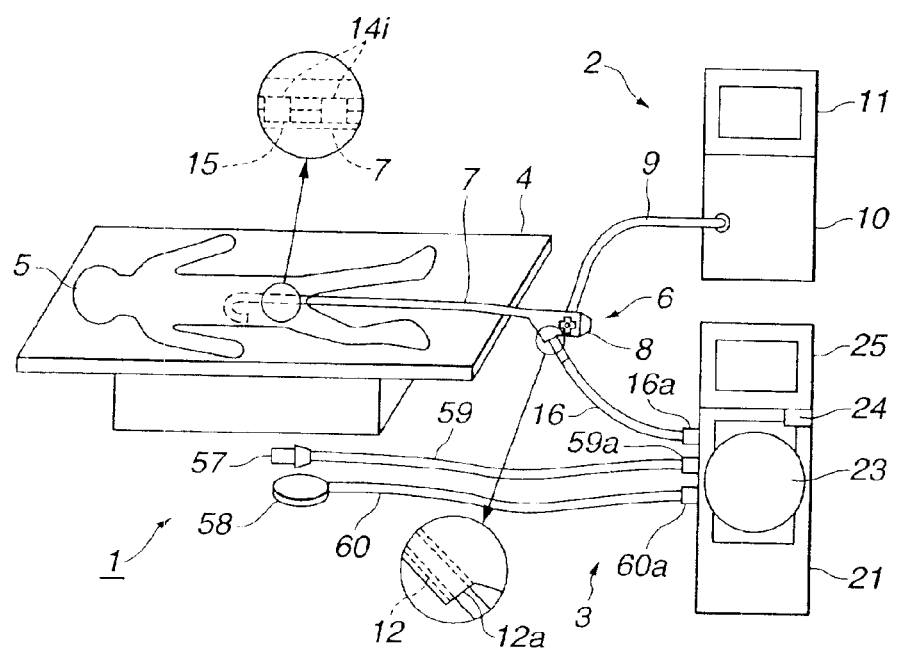

Referring to FIG. 1, an endoscope system 1 according to the present embodiment comprises an endoscope device 2 that performs an endoscopy, and an endoscope shape detector 3 used for supplementing an endoscopy, and this endoscope shape detector 3 is used as an auxiliary means when the inserted portion 7 of a video endoscope 6 is inserted into the body cavity of a patient 5 lying on a bed 4 and an endoscopy is performed.

In the video endoscope 6, an operation portion 8 wherein a curved operation knob is provided at the rear end of the elongated inserted portion 7 with flexibility is formed. A universal cord 9 is extended from this operation portion 8 and connected to a video imaging system (or a video processor) 10.

The video endoscope 6 transmits illuminating light from a light source portion in the video processor 10 through which a light guide is passed, and emits the illuminating light transmitted through an illumination window provided at the front end of the inserted portion 7, thereby illuminating an affected part and others. Subjects such as the illuminated affected part forms an image on an image-forming element disposed at the image-forming position thereof by an objective lens attached to an observation window provided adjacent to the illumination window, and this image-forming element photoelectrically converts the image.

The photoelectrically converted signals is subjected to signal-processing by an image signal processing block within the video processor 10, and standard image signals are produced, which are displayed on an image observation monitor 11 connected to the video processor 10.

The video endoscope 6 has a forceps channel 12, and from the insertion opening 12a of this forceps channel 12, a probe 15 having, for example, sixteen magnetism generating elements (or source coils) 14a, 14b, . . . , 14p (hereinafter, representatively expressed by reference numeral 14i) are passed through, thereby providing source coils 14i within the inserted portion 7.

A source cable 16 extended from the rear end of the probe 15 is arranged so that a connector 16a disposed at the rear end of the source cable 16 is detachably connected to a detecting unit 21 as a main body of the endoscope shape detector 3. A high-frequency signal (drive signal) is applied to the source coils 14i as magnetism generating means from the detecting unit 21 side via the source cable 16 as high-frequency signal transmitting means, and thereby the source coils 14i radiate electromagnetic waves with magnetic fields into the surroundings.

Figure 2:
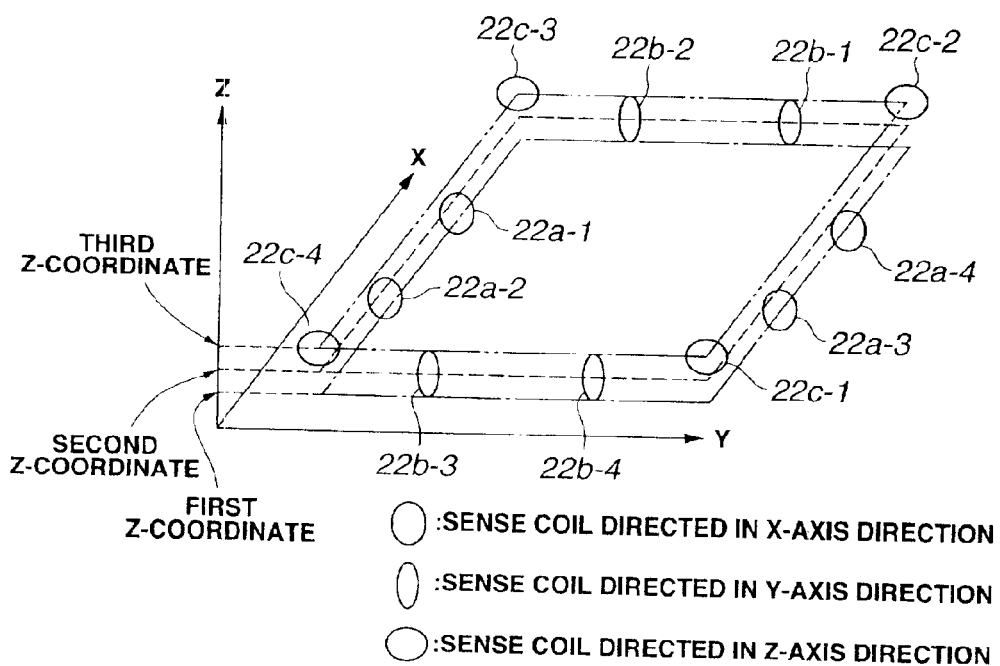

The detecting unit 21 disposed in the vicinity of the bed 4 on which the patient 5 is lying is provided with a sense coil unit 23 so as to be vertically movable (ascent and descent), and the sense coil unit 23 has a plurality of sense coils disposed therein. More specifically, as shown in FIG. 2, the following twelve sense coils are disposed: sense coils such that the Z-coordinate of the center thereof is a first Z-coordinate, for example, sense coils 22a-1, 22a-2, 22a-3, and 22a-4 that are directed to the X-axis, sense coils such that the Z-coordinate of the center thereof is a second Z-coordinate different from the first Z-coordinate, that is, sense coils 22b-1, 22b-2, 22b-3, and 22b-4 that are directed to the Y-axis, and sense coils such that the Z-coordinate of the center thereof is a third Z-coordinate different from the first and second Z-coordinates, that is, sense coils 22c-1, 22c-2, 22c-3, and 22c-4 that are directed to the Z-axis. Hereinafter, these sense coils are representatively expressed by reference numeral 22j.

The sense coils 22j are connected to the detecting unit 21 via a cable (not shown) from the coil unit 23. The detecting unit 21 has an operation panel 24 for a user to operate this unit. Also, in the detecting unit 21, a liquid-crystal monitor 25 as display means displaying a detected endoscope shape, is disposed at an upper portion thereof.

Figure 3:
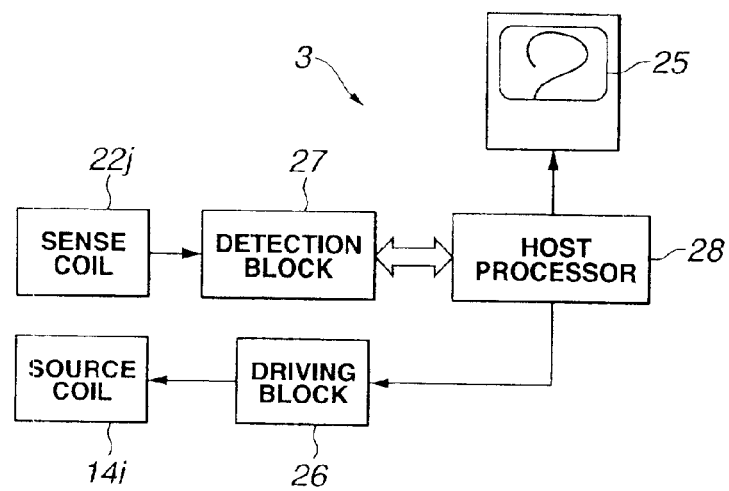

As shown in FIG. 3, the endoscope shape detector 3 comprises a driving block 26 that drives the source coils 14i, a detecting block 26 that detects signals received by the sense coils 22j within the coil unit 23, and a host processor 28 that signal-processes signals detected by the detecting block 27.

As shown in FIG. 4A, within the probe 15 disposed at the inserted portion 7 of the video endoscope 6, sixteen source coils 14i are arranged with a predetermined spacing thereamong as described above, and these source coils 14i are connected to a source coil drive circuit 31 that constitutes the driving block 26 and that produces sixteen high-frequency signals that are different from one another.

The source coil drive circuit 31 drives the source coils 14i by sinusoidal drive signal currents having different frequencies from one another. The respective drive frequencies are set by drive frequency setting data (that is, drive frequency setting data) stored in drive frequency setting data storage means or drive frequency setting data memory means (not shown) within the source coil drive circuit 31. These drive frequency data are stored in drive frequency data storage means (not shown) within the source coil drive circuit 31 by a CPU (central processing unit) 32 performing calculation processing of the endoscope shape in the host processor 28, via PIO (parallel input/output circuit) 33.

On the other hand, the twelve sense coils 22j within the coil unit 23 are connected to a sense coil signal amplifying circuit block 34 constituting the detecting block 27.

As shown in FIG. 5, in the sense coil signal amplifying circuit block 34, twelve single-core coils 22k constituting sense coils 22j are connected to respective amplifying circuits 35k, thereby providing twelve processing systems. Minute signals detected by the single-core coils 22k are amplified by the respective amplifying circuits 35k, and unwanted components are removed via respective filter circuits 36k that have pass bands where a plurality of frequencies generated by the source coil group passes. These signals are outputted to respective output buffers 37k, and then, in respective ADCs (analog/digital converters) 38k, they are converted into digital signals that can be read by the host processor 28.

The detecting block 27 comprises the sense coil signal amplifying circuit block 34 and the ADCs 38k, and the sense coil signal amplifying circuit block 34 comprises the amplifying circuits 35k, the filter circuits 36k, and the output buffers 37k.

Returning to FIG. 4A, the twelve-system outputs of the sense coil signal amplifying circuit block 34 are transmitted to the twelve ADCs 38k, and are converted into digital data having a predetermined sampling period by a clock supplied from a controlled signal generating circuit block 40. These digital data are written into a two-port memory 42 by a control signal from the controlled signal generating circuit block 40 via a local data bus 41.

Figure 6:
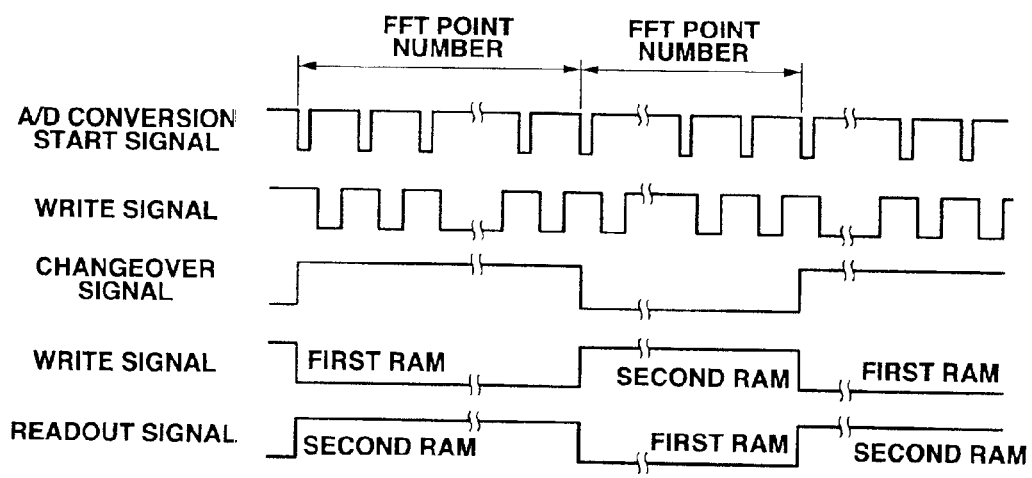

As shown in FIG. 5, the two-port memory 42 is functionally constituted of a local controller 42a, a first RAM 42b, a second RAM 43c, and a bus switch 42d. By the timings as shown in FIG. 6, the ADCs 38k start an A/D conversion by an A/D conversion signal from the local controller 42a, and, while the bus switch 42d switches between the RAMs 42b and 42c by a switching signal from the local controller 42a, the first RAMs 42b and 42c are alternately used as an readout memory and a write memory. After power-on, data fetching is performed at all times, by a write signal.

Returning again to FIG. 4A, the CPU 32 reads an internal digital data written into the 2-port memory 42 by a control signal from the controlled signal generating circuit block 40, via a bus 46 comprising a local data bus 43, a PCI controller 44, and a PCI bus 45 (see FIG. 5), and performs a frequency extraction processing (fast Fourier transformation: FFT) with respect to the digital data using a main memory 47, as will be described later. Thereby, the digital data is separated and magnetic-field detection information of a frequency component corresponding to the drive frequency of each of the respective source coils 14i is extracted, and from the separated digital data of the magnetic-field detection information, the spatial position coordinate of each of the source coils 14i provided in the inserted portion 7 of the video endoscope 6 is calculated.

Also, from the calculated position coordinate data, an insertion state of the inserted portion 7 of the video endoscope 6 is estimated, then display data forming an endoscope shape image are produced and outputted to a video RAM 48. A video signal generating circuit 49 reads the data written into the video RAM 48, then converts it to an analog video signal, and outputs it to the liquid-crystal monitor 25. With the analog video signal inputted, the liquid-crystal monitor 25 displays an insertion shape of the inserted portion 7 of the video endoscope 6.

In the CPU 32, magnetic-field detection information corresponding each of the source coils 14i, that is, an electromotive force (amplitude value of a sinusoidal signal) generated in the single-core coils 22k constituting the sense coils 22j, and phase information are calculated. Here, the phase information refers to the polarity "±" of the electromotive force.

As shown in FIG. 1, this embodiment is arranged so that the detecting unit 21 can use an extracorporeal marker 57 and a reference plate 58 as an endoscope auxiliary equipment.

Specifically, in the detecting unit 21, the extracorporeal marker 57 for displaying the extracorporeal position thereof in order to check the position of the inserted portion 7 of the video endoscope 6 inserted into a body cavity, and the reference plate 58 used for displaying an endoscope insertion shape at all times from a specific direction (of the patient 5) even though the body posture of the patient 5 changes, for example, by attaching to the abdomen or the like of the patient 5, can also be used by connecting to the detecting unit 21.

The extracorporeal marker 57 has a single source coil stored therein, and a connector 59a at the base end of the cable 59 of the extracorporeal marker 57 is detachably connected to the detecting unit 21.

By connecting this connector 59a to the detecting unit 21, the source coil in the extracorporeal marker 57 is driven in the same manner as the source coils in the probe 15, and thereby the position of the source coil of the extracorporeal marker 57 detected by the coil unit 23 is displayed on the monitor 25, as in the case of the endoscope insertion shape.

The reference plate 58 is arranged so that, for example, three source coils are arranged inside the disk-shaped portion thereof and on the disk surface thereof, and the connector 60a at the base end of the cable 60 is detachably connected to the detecting unit 21.

By the position detection of the three source coils, the surface on which they are arranged is determined. For example, these coils are used for rendering the image of the inserted portion so that image becomes an insertion shape when viewing the inserted portion 7 from the direction perpendicular to the above-described surface.

As sown in FIG. 4A, in the present embodiment, the detecting unit 21 has connector receptacles 21a, 21b, and 21c to which the connector 16a for the probe 15, the connector 59a for the extracorporeal marker 57, and the connector 60a for the reference plate 58 are connected, respectively. The connector receptacles 21a, 21b, and 21c are connected to the source coil drive circuit 31.

As shown in FIG. 4B, for example, the connector receptacle 21a has a connection detecting mechanism 80 that detects the presence/absence of the connection of the connector 16a.

Within the connector 16a, there are provided connection pins p1 to pn to be connected to the source coils 14a to 14p, respectively, and in addition, a common pin pc and a connection detection pin pk are provided. Here, the pin pk is connected to the pin pc.

On the connector receptacle 21a side, there are provide pin receptacles p1' to pn' to be connected to the connection pins p1 to pn, respectively, and pc' and pk' corresponding to the common pin pc and the connection detection pin pk, respectively. Here, the pin receptacle pc' is connected to the ground.

The pin receptacle pk' is connected to a power supply end Vc via a pull-up resistance R, and also to a connection detection port of the CPU 32. The CPU 32 determines whether the probe 15 is in a non-connected state or a connected state to the detecting unit 21, based on whether the level of the pin receptacle pk' is in a "H" level, which is a power supply end Vc level, or "L" level, which is the ground level.

More specifically, as shown in FIG. 4B, when the probe 15 is connected to the detecting unit 21, the pin receptacle pk' is connected to the pin receptacle pc' connected to the ground via the conducting pins pk and pc on the connector side 16a, and therefore, the level of the pin receptacle becomes "L" level of the ground, whereby the CPU 32 determines the probe 15 to be in a connected state.

On the other hand, when the probe 15 is in a non-connected state, the level of the pin receptacle becomes "H" level of the power supply end Vc, whereby the CPU 32 determines the probe 15 to be in a non-connected state.

Figures 14A, 14B:
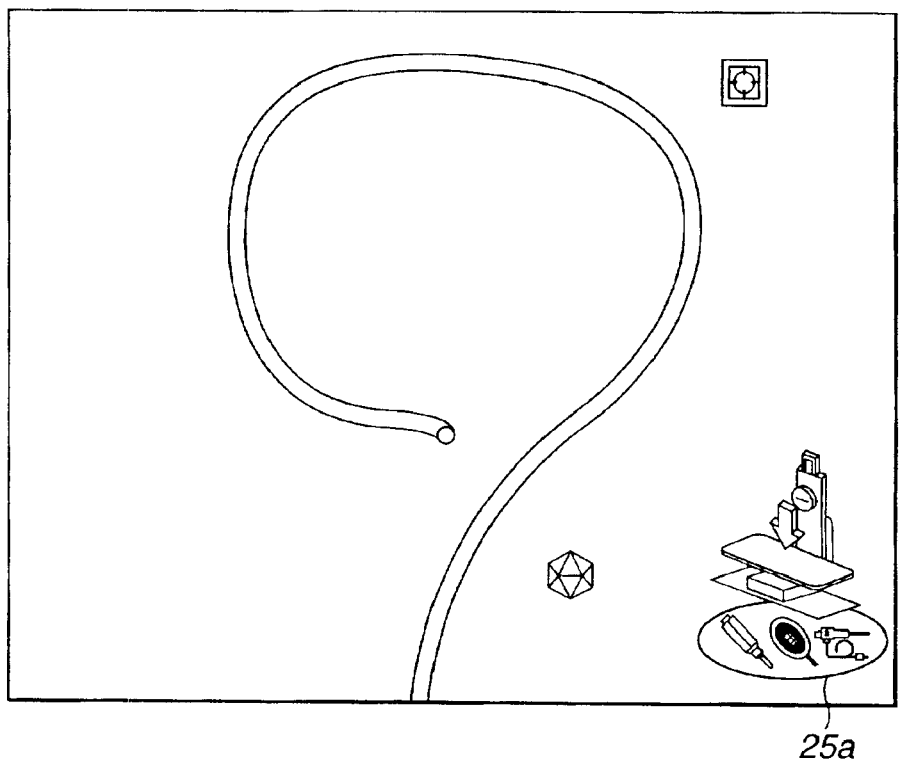
FIGS. 14A and 14B, respectively, are views showing connection display functions and the forms of connection state displays when the endoscope and others are connected to the detecting unit.

The connector receptacle 21b and 21c has also connection detecting mechanism 80 as in the case of the connector receptacle 21a. When the probe 15 (or the endoscope having it), the extracorporeal marker 57, and the reference plate 58 are connected to the detecting unit 21, the CPU 32 displays an endoscope connection icon, an extracorporeal marker connection icon, and a reference plate connection icon on, for example, a connection state displaying block 25a situated at the lower right corner of the monitor 25 in FIG. 14A shown later. When these are not connected to the detecting unit 21, the CPU 32 does not display the icons.

Also, in this embodiment, the CPU 32 has the function of determining means 32a that determines, based on the detected outputs from the sense coils 22j, whether the position of each the source coils is in an effective detection range.

The determining means 32a firstly compares, with a predetermined reference value, the electromotive force detected by the sense coils 22j, which detect magnetic field generated by the source coils 14i (including the source coils of the extracorporeal marker 57 and reference plate 58 beside the source coils 14i in the probe 15). Based on the comparison results, the determining means determines whether the number of the detected output values exceeding the reference value is not less than a predetermined number and, by virtue of the detected outputs thereof, the positions of the source coils 14i are in an effective detection range in which they can be detected with an accuracy not lower than a predetermined accuracy, or the positions of the source coils 14i are outside the effective detection range in which they cannot be detected with an accuracy not lower than the predetermined accuracy because the number of the detected output values exceeding the reference value is less than the predetermined number.

The determination results are displayed so as to be understandable to the operator by changing the display form according to the determination results, when an endoscope insertion shape and three-dimensional positions of the extracorporeal marker 57 are displayed.

For example, in the case of the extracorporeal marker 57, when the position of the source coil therein can be detected with an accuracy not lower than a predetermined accuracy, the marker display color displaying the extracorporeal marker 57 is changed on the monitor 25. In the case of the reference plate 58, the display form is changed by changing the display color depending on whether the surface thereof can be determined with an accuracy not lower than a predetermined accuracy by position detection of the plurality of source coils stored in the reference plate 58.

For this purpose, for example, when the above-described endoscope connection icon, the extracorporeal marker connection icon, and the reference plate connection icon are to be displayed, the CPU 32 performs a display control with respect to the monitor 25 through the function of display color selecting means 32b, based on the determination results. The operator, therefore, can easily recognize, from the display colors of the icons displayed on the connection state display portion 25a situated in the lower right part in FIG. 14A, whether the endoscope shape, the extracorporeal marker, and the reference plate are in states detected with an accuracy not lower than the predetermined accuracy.

Furthermore, in this embodiment, in addition to performing a display by changing display color on the connection state displaying block 25a, the insertion shape and the marker position display of the extracorporeal marker 57 displayed on the monitor 25 are also arranged to change the display color thereof depending on whether the insertion shape and the position of the extracorporeal marker 57 are in an effective detection range.

For example, in the case of the probe 15 (and hence, the endoscope 6), since the insertion shape thereof is displayed using interpolation or the like based on the position detection of the source coils 14i, for example, the insertion shape portion present in the effective detection range and that present outside the effective detection range are displayed using display colors different with each other.

To this end, the determination result by the above-described determining means 32a is arranged so as to be reflected to image data to be stored in e.g., a video RAM 48. That is, when the CPU 32 is to store image data such as insertion shapes and the like in the video RAM 48, the CPU 32 stores them in R, G, and B planes according to the determination results.

For example, when the entire insertion shape displayed on the monitor 25 is in the effective detection range, in order to display image data thereof in a predetermined color, for example, in green color, the image data thereof are stored in the G plane of the video RAM 48.

On the other hand, when one portion of the insertion shape is outside the effective detection range, in order to display image data of the portion in, for example, yellow color, the image data thereof are stored in the G and R planes of the video RAM 48.

Figure 14C:
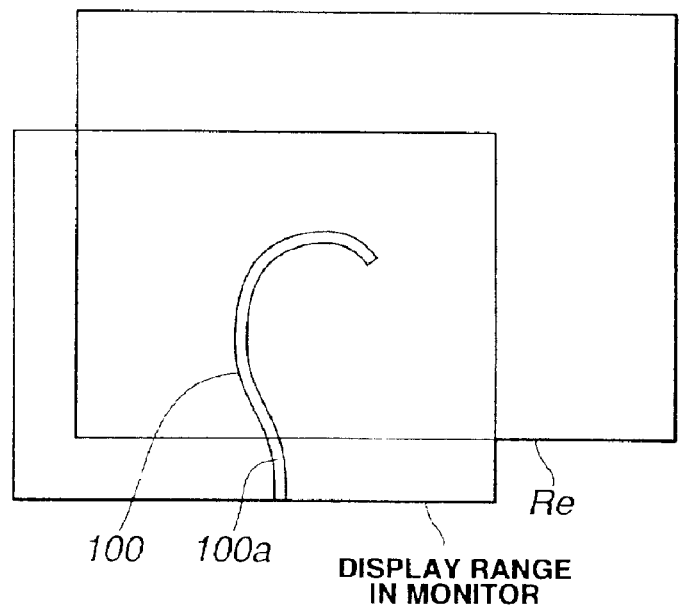
FIG. 14C is a view explaining the case where a portion of the endoscope insertion shape displayed on a monitor falls out of an effective detection range, and 14D is a view explaining data to be stored in R and G planes in the case of FIG. 14C.

As a specific example, FIG. 14C shows the case where the major portion 100 of the insertion shape displayed on the monitor 25 is inside the effective range Re, while the one portion 100a thereof is outside the effective range Re.

Figure 14D:
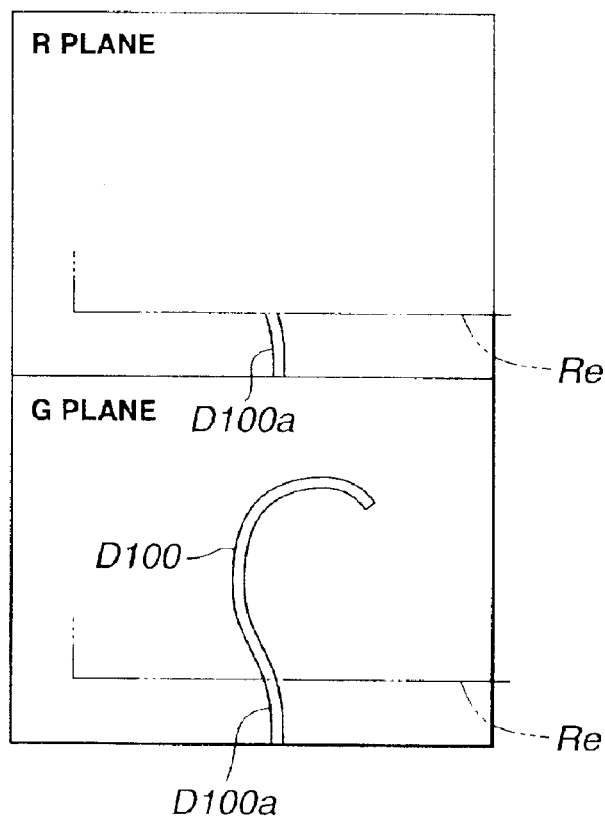

The determining means 32a stores the data of the inserted portion shape in the R, G, and B planes of the video RAM 48 according to the determination results, as shown in FIG. 14D. Specifically, the data D100 of the major portion 100 of the insertion shape (the portion determined to be inside the effective range Re) are stored only in the G plane, while the data D100a of the one portion 100a determined to be outside the effective range Re are stored in the R and G planes. The major portion 100 determined to be inside the effective range Re are displayed in green color, while the one portion 100a determined to be outside the effective range Re is displayed in yellow color.

Substantially similarly, the extracorporeal marker 57 is also arranged so as to change the marker color displaying the extracorporeal marker 57, according to whether the extracorporeal marker 57 is in the effective detection range.

In this manner, the present embodiment is characterized in that, the operator can easily recognize, from the insertion shape and the display color of the extracorporeal marker 57 and the like displayed on the monitor 25, whether they are in the effective detection range, and whether they are in a state detectable with an accuracy not lower than the predetermined accuracy, or an accuracy lower than the predetermined accuracy.

Even when the probe 15 is in a connected state, or the source coil side is actuated, if a detection signal cannot be detected by the sense coils, it is determined that the sense coils are out of order.

Figure 7B:
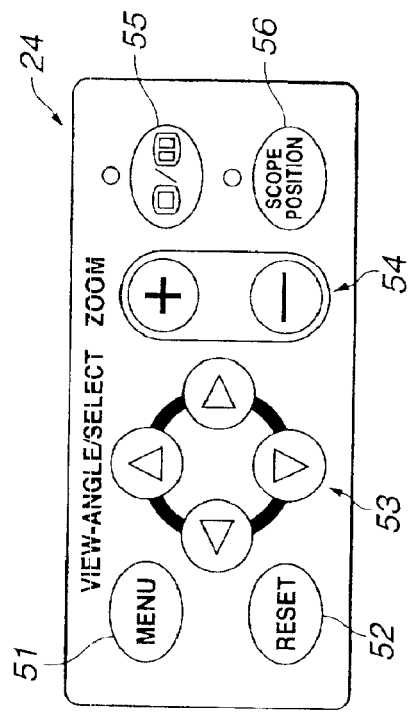
FIGS. 7A to 7C are views showing a detecting unit, the configuration of an operation panel, and an display example of menu, respectively.
Figure 7C:
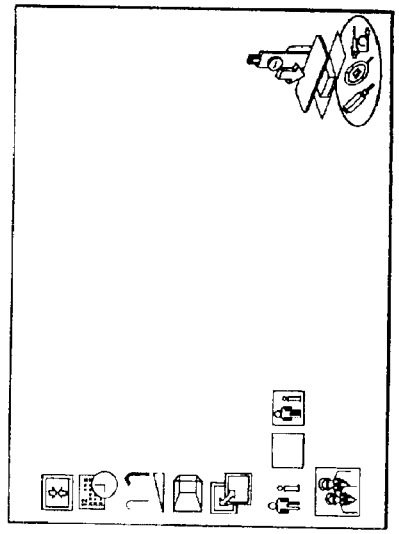
Figure 7A:
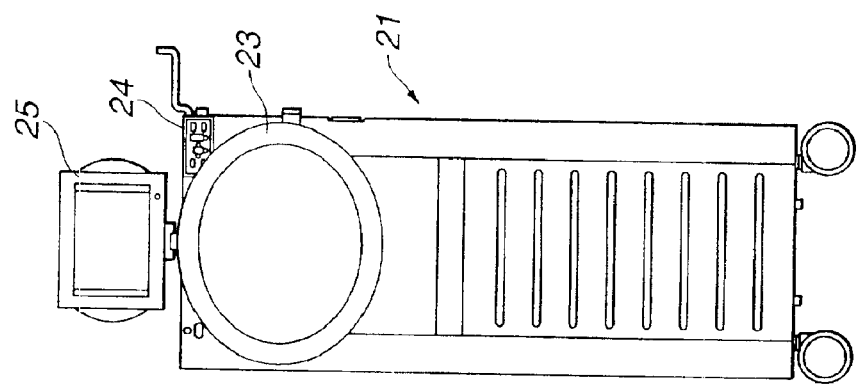

FIGS. 7A and 7B show the detecting unit 21 and an operation panel 24 therein. As shown in FIG. 7B, this operation panel 24 comprises a menu button 51 for displaying menu bar (of the main menus shown in the left corner shown in FIG. 7C), a reset button 52 for performing a reset operation, a view-angle/select button 53 that changes the view angle by rotating the endoscope insertion shape using up and down arrows and right and left arrows, and that performs a function selection (up and down arrows) and item selection (right and left arrows) (hereinbefore, for simplification, descriptions may be made using ↑↓ buttons and ←→ buttons), a zoom button 54 that performs the enlargement/reduction and the changes in date, time, and area, and that performs displays using + and − (hereinafter, descriptions may made using a + button and a − button), a one-screen/two-screen button 55 that provides instruction for displays by one screen or two screen, and a scope position button 56 that sets the start position of the display of the endoscope insertion shape.

More detailed functions are a follows.

(a) Function of the Menu Button 51:

The menu bar is caused to be displayed or non-displayed at a specified position. (When the menu bar 50 is caused to be non-displayed, the state of the set function is stored in a storage device.

Selection of items on a date, time, and area setting screen.

(b) Functions of the Reset Button 52:

In the state wherein the function of each item has been set by the menu bar, the set value of each menu item is returned to the value before the menu bar is displayed.

On the date, time, and area setting screen, the set value of the function of each item is returned to the value before the date, time, and area setting screen is displayed.

(c) Functions of the View-angle/Select Button 53:

Using ←↑↓→ the buttons, rotation of the endoscope insertion shape;

Using the ↑↓ buttons, movement of the select items in the menu bar;

Using the ←→ buttons, display and selection of sub-menus; and selection of the functions of the items selected by the menu button 51 on the date, time, and area setting screen.

(d) Functions of the Zoom Button 54:

Enlargement/reduction of the endoscope insertion shape;

Setting of the functions of the items on the date, time, and area setting screen.

(e) Function of the One-screen/Two-screen Button 55:

Display of two screens mutually different in viewpoint-position/orientation.

(f) Function of the Scope Position Button 56:

Setting such that the extracorporeal marker 57 is brought to the position from which the display of the anal position or the like of a patient is to be started, and that the display is started from that position by operating the scope position button 56.

Next, operation by the operation panel 24 will be described.

[Case Where the Main Menu (Function) is Selected]

The menu bar shown in FIG. 7C is displayed on the monitor 25 by the operation of the menu button 51. When the menu bar is displayed in this manner, if the menu button 51 is again operated, the menu bar comes into a non-display state. At this time, the functional item changed takes effect.

When the menu bar is displayed, it is scrolled by the ↑↓ buttons in the arrow directions thereof, and the button positions indicated by square frames comes into a selected state.

FIG. 10 shown later illustrates details of the icons of the menu items by the menu bars in FIG. 7C, and the sub-menu items thereof and functions thereof.

When the reset button 52 is selected, all functional items changed are cancelled. Simultaneously, the menu bar comes into a non-display state. By a preset button, the setting can be returned to that when the device is factory-shipped.

[Case Where the Sub-Menu is Selected]

In the state wherein the function selecting icon is in a selected state, when the → button is selected, the sub-menu thereof is displayed.

The movement between items is performed by the ←→ buttons.

The icon in a selected state represents an item that is now effective.

The determination of item selection is performed by the menu button 51, and a temporary determination is performed at the point of time when a function selection is performed by the ↑↓ buttons.

Next, reference will be made of the change of displaying method for the endoscope insertion shape by the operation panel 24.

(1) Enlargement/Reduction of the Endoscope Insertion Shape by the Zoom Button 54 a) When pushing "+" of the zoom button 54 on the operation panel 24 of the detecting unit 21, an operation notice symbol for enlargement is displayed on a specified position on the monitor screen 25, and the endoscope insertion shape is enlarged.

b) When pushing "−" of the zoom button 54 on the operation panel 24 of the detecting unit 21, an operation notice symbol for reduction is displayed on a specified position on the monitor screen 25, and the endoscope insertion shape is contracted.

(2) Rotation of the Endoscope Insertion Shape by View-angle/Select Button 53 a) When pushing "←" of the view-angle/select button 53 on the operation panel 24 of the detecting unit 21, an operation notice symbol for left rotation is displayed on a specified position on the monitor screen 25, and the endoscope insertion shape is rotated left.

b) When pushing "→" of the view-angle/select button 53 on the operation panel 24 of the detecting unit 21, an operation notice symbol for right rotation is displayed on a specified position on the monitor screen 25, and the endoscope insertion shape is rotated right.

c) When pushing "↑" of the view-angle/select button 53 on the operation panel 24 of the detecting unit 21, an operation notice symbol for upward rotation is displayed on a specified position on the monitor screen 25, and the endoscope insertion shape is rotated upward.

d) When pushing "↓" of the view-angle/select button 53 on the operation panel 24 of the detecting unit 21, an operation notice symbol for downward rotation is displayed on a specified position on the monitor screen 25, and the endoscope insertion shape is rotated downward.

[Change of Displaying Method for the Endoscope Insertion Shape by the Operation Panel 24 (Except for Date, Time, and Area Setting)]

a) By pushing the menu button 51 on the operation panel 24 of the detecting unit 21, the menu bar is displayed on the left side of the monitor screen 25.

b) By pushing "↑" or "↓" of the view-angle/select button 53 on the operation panel 24 of the detecting unit 21, a movement to an item requiring a change is performed.

c) By pushing "→" or "←" of the view-angle/select button 53 on the operation panel 24 of the detecting unit 21, an item is selected, and the sub-menu of the selected function is displayed.

d) The item of the displayed sub-menu is set by pushing "→" or "←" of the view-angle/select button 53 on the operation panel 24 of the detecting unit 21.

e) When changing the setting of another function, the item is moved to another item and a required function is selected by pushing "↑" or "↓" of the view-angle/select button 53 on the operation panel 24 of the detecting unit 21. For function setting, (c) and (d) are performed.

f) When function setting has been completed, the menu bar is made to be in a non-display state by pushing the menu button 51 on the operation panel 24 of the detecting unit 21, and thus the setting by the menu bar is completed.

[Change of Displaying Method for the Endoscope Insertion Shape by the Operation Panel 24 (Setting of Date, Time, and Area)]

a) By pushing the menu button 51 on the operation panel 24 of the detecting unit 21, the menu bar is displayed on the left side of the monitor screen 25.

b) By pushing "↑" or "↓" of the view-angle/select button 53 on the operation panel 24 of the detecting unit 21, movements to the set items of data and area are performed.

c) By pushing "→" or "←" of the view-angle/select button 53 on the operation panel 24 of the detecting unit 21, set items of date, time, and area are selected, and the sub-menu of the setting of date, time, and area are displayed.

d) By pushing the menu button 51 on the operation panel 24 of the detecting unit 21, a required sub-menu item is selected.

e) By pushing "→" or "←" of the view-angle/select button 53 on the operation panel 24 of the detecting unit 21, a function to be set, of the sub-menu item is selected.

f) By pushing "+" or "−" of the zoom button 54 on the operation panel 24 of the detecting unit 21, setting of a function is performed.

g) When setting of the item of another sub-menu, a required submenu item is selected by pushing menu button 51 on the operation panel 24 of the detecting unit 21, and function setting is performed by (e) and (f).

h) When function setting has been completed, the state is returned to the state set by menu bar, by pushing "↑" or "↓" of the view-angle/select button 53 on the operation panel 24 of the detecting unit 21. Then, the menu bar is made to be in a non-display state by pushing the menu button 51 on the operation panel 24 of the detecting unit 21, and thus the setting by the menu bar is completed.

Figure 8:
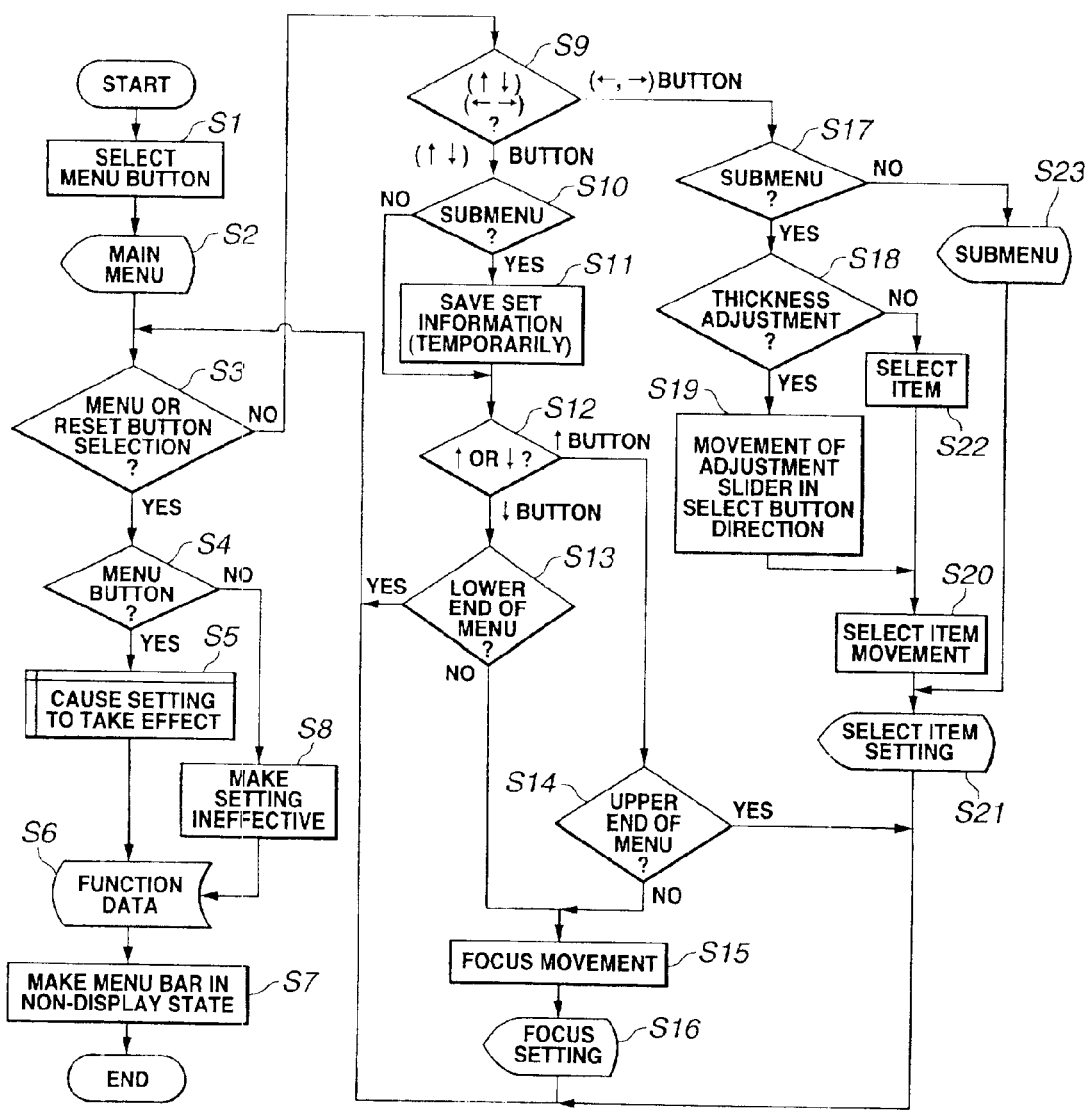

Next, a representative example of main operation will be specifically described with reference to a flowchart thereof shown in FIG. 8.

When the detecting unit 21 is powered up and is in a ready-to-use state, by selectively operating the menu button 51 as shown in step S1, the main menu of step S2 is displayed on the monitor 25.

At next step S3, it is determined whether the menu button 51 or the reset button 52 has been selectively operated, and if the menu button 51 has been selectively operated, it is determined whether the menu button 51 has been selectively operated, at next step S4. If so, a state such that the setting by the above-mentioned selection takes effect is produced at step S5, and the function data thereof is stored at step S6. Then, by making the menu bar non-displayed at step S7, the processing is completed. On the other hand, when the menu button 51 is not selectively operated, the setting is made ineffective at step S8, and the processing moves to step S5.

When, at step S3, neither the menu button 51 nor the reset button 52 has been selectively operated, it is determined, at step S9, whether any one of the ↑↓ buttons and the ←→ buttons has been selectively operated.

When the ↑↓ buttons are selectively operated, it is determined whether the menu is a sub-menu, at step S10. If so, after a set information is saved at step S11, the processing moves to step S12, and if not so, the processing straight moves to step S12 skipping step S11.

At step 12, it is determined whether either of the ↑↓ buttons has been operated, and if the ↓ button has been operated, it is determined, at step S13, whether the button has fallen at the end of the menu. If so, the processing moves to step S3.

At step S13, if the button has not been fallen at the lower end of the menu, the processing moves to step S15, at which a focus movement is performed by the ↓ button, and focus setting is performed at step S16.

If, in the determination at step 12, the ↑ button has been operated, it is determined whether the button has fallen at the upper end of the menu, and if so, the processing moves to step S3, and if not so, the processing moves to step S15.

On the other hand, in the determination at step 9, if the ←→ buttons have been selectively operated, it is determined whether the sub-menu has been selected, at step S17, and if so, it is determined whether the sub-menu corresponds to thickness adjustment, at step S18. If so, an adjustment slider movement in the arrow direction of the select button is performed at step S19, and further a movement of the select item is performed at step S20. Subsequently, a select item is set, and then the processing returns to step S3.

At step S18, if the sub-menu is not a thickness adjustment, setting of a select item is performed, and then the processing moves to step S20.

In the determination at step S17, if the menu is not a sub-menu, a display of sub-menu is performed at step S23, and then the processing moves to step S21.

Next, representative operation of the date, time, and area setting will be described with reference to a flowchart thereof shown in FIG. 9A.

Figure 9A:
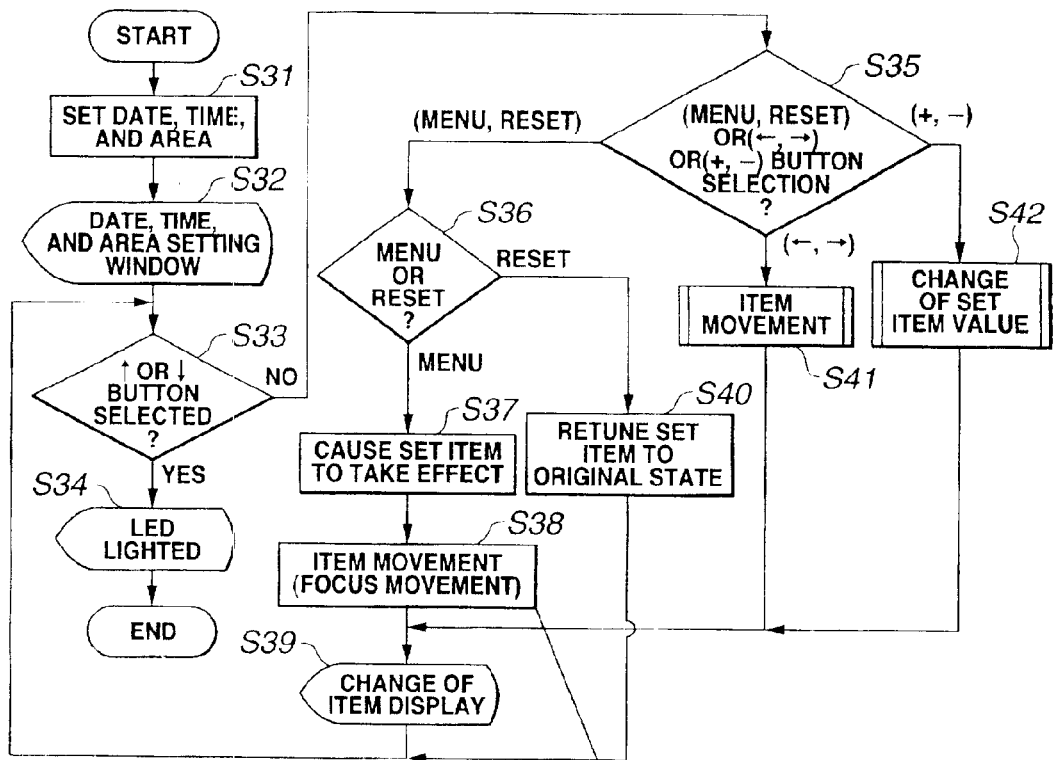
FIGS. 9A and 9B, respectively, are a flowchart and an operational view explaining the operations of the setting of date, time, and area.

When the detecting unit 21 is powered up into a ready-to-use state, and the operation of date, time, and area setting at step S31 shown in FIG. 9A is performed a date, time, and area setting window is displayed at a subsequent step S32.

At step S33, it is determined whether the ↑ or ↓ button has been operated, and if so, in step S34, the processing moves to the next select item, and by lighting an LED, the processing is completed.

In the determination at step S33, if neither the ↑ button nor the ↓ button has not been selectively operated, it is determined, at step S35, whether any of (menu and/or reset), (← and/or →), and (+ and/or −) buttons has been selected.

If it is determined that the (menu and/or reset) buttons has been selected, it is further determined, at step S36, whether either of the menu button 51 and the reset button 52 has been selected. If the menu button 51 has been selected, the select item in step S37 is caused to take effect. At the subsequent step S38, a movement to a desired item from the set item is performed. After the desired item has been set, the change of item display is performed at step S39, and the processing returns to step S33. On the other hand, if it is determined, at step S36, that the reset button 52 has been selected, the set item is returned to the original state at step S40, and the processing returns to step S33.

Figure 9B:
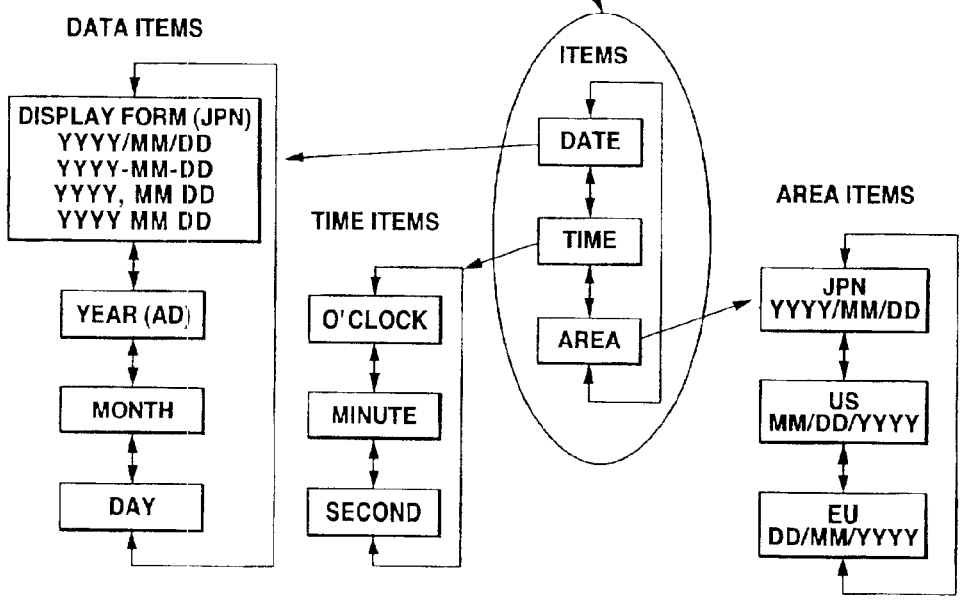

FIG. 9B shows the details of the item movement at step S38. Referring to FIG. 9B, in the items of date, time, and area, the position of a select item can be vertically moved by the ↑ or ↓ button, and more detailed setting can be performed in the selected item.

For example, when attempting to change the time, setting is performed in the time item by the menu button 51, and the item of the time to be set is selected by operating the ← and/or → buttons. Then, the value of the time is set by operating the + and/or − button, and further the items of minute and second are selectively operated. Other date item and area item can be selectively operated in substantially the same manner as the foregoing.

If it is determined, at step S35, that the (← and/or →) buttons has been selected, an item movement is performed at step S41, and the processing moves to S39. If it is determined, at step S 35, that the (+ and/or −) buttons have been selected, the value of the set item is changed at step S41, and the processing moves to S39.

Figure 16:
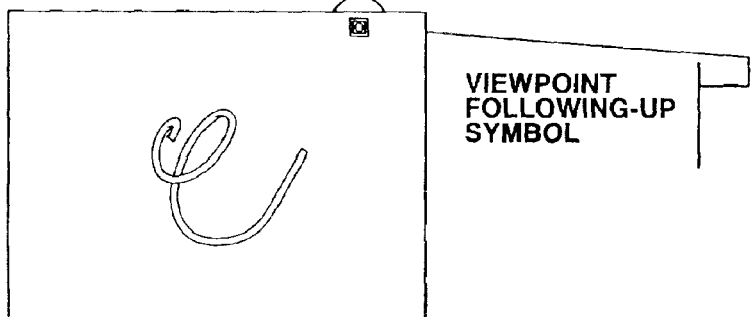
Figure 17:
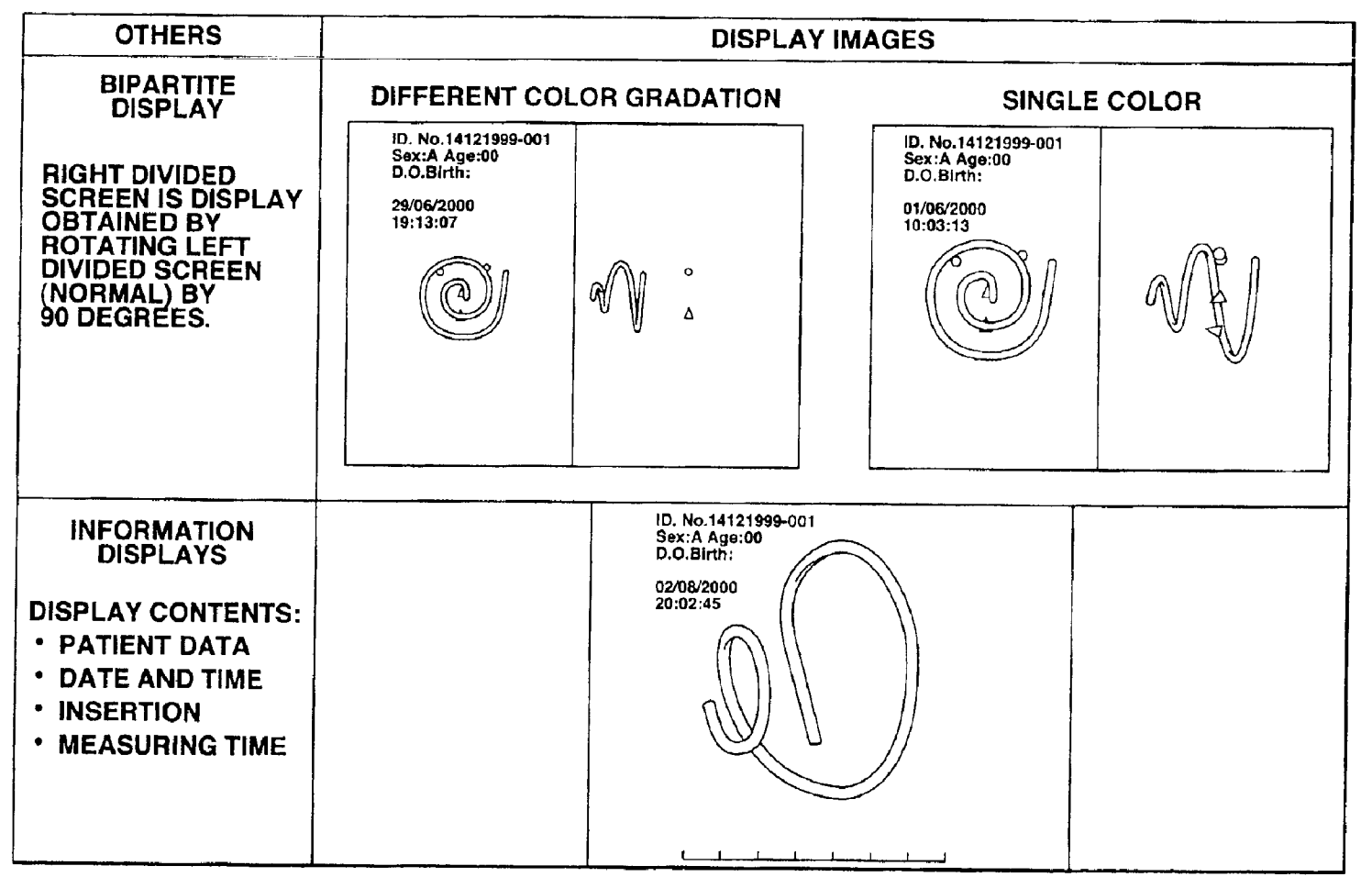

FIG. 10 provides a summary of main menu bar icons and the functions thereof. FIGS. 15 and 16 provide summaries of operation notice symbols and the functions thereof, and FIG. 17 shows other display functions.

For example, representative menu icons are described below. As shown in FIG. 10, in the first row in the menu, a set menu and an icon therebelow are shown, and on the right side thereof, set contents (sub-menu) that can be selectively set, and sub-menu icons corresponding to the set contents are shown. Also, in a remarks column on the right side thereof, function (remarks) is written.

Specifically, a first set menu in FIG. 10 is a menu for performing a display mode changeover, and can perform setting (selection) of displaying the endoscope inserted shape from above and below.

More specifically, with the icon of this display mode changeover menu designated, by selecting one of the two submenu icons on the right side by ← and/or → buttons, a mode corresponding to the selected icon can be selected, out of the mode in which the insertion form is displayed from above and the mode in which the insertion form is displayed from below.

The icon in the next menu and sub-menu show a date and time setting menu, the icon thereof, a sub-menu that can be set by the time setting menu thereof, and so on.

By this date and time setting menu, selection of a display format and setting of data and time can be performed.

A third menu is a scope model thickness-adjustment menu, and by the use of the sub-menu thereof, the thickness of the scope mode can be increased by moving the position of an index to the right, while the thickness of the scope mode can be reduced by moving the position of an index to the left.

A fourth menu is a perspective changeover menu with its icon therebelow, and by the submenu thereof, a rendering mode can be selectively set, out of a mode with a perspective and a mode without a perspective.

A fifth menu is a background changeover menu, and by the submenu thereof, a background color can be selectively set out of a background color that is a single color of blue-green, and a background color that is displayed by blue-purple color gradation.

A sixth menu is a display changeover menu, and by the submenu thereof, a display mode can be selected out of a display mode with an information display and a display mode without information display. In this case, the information refers to, for example, patient data, dates, times, display lengths, and gages.

A seventh menu is a menu for performing the registration and restore of screen setting, and by the use of this menu, the set contents set by the above-described display mode changeover menu or the like, and the magnification ratio and rotation amount of the scope model are registered and restored to suit the preferences of the user.

Next, more specific descriptions of the registration of screen setting, the restore, and the deletion will be made with reference to FIGS. 11A to 13C.

The state set by a menu, and the rotation amount of the scope model and the magnification and demagnification ratios thereof, which are set by the operation panel 24, can be registered, restored, and deleted to suit the preferences of the user. Hereinafter, the registration, restore, and deletion are sequentially described.

(a) Registration

By selecting the icon of the registration of screen setting, and that of the restore menu, the registration of screen setting, and the restore menu shown in FIG. 11A are brought into a display state. In this display state, for example, numbers 1 to 5 are displayed, so that each set item can be registered with one of these number. The set contents with the numbers are displayed by respective corresponding icons.

Next, in the state shown in FIG. 11A, a cursor is moved to a number to be registered by operating the by ← and/or → buttons. Thereafter, the number to be registered as an operation of pushing the ↑ or ↓ button is determined. Thereupon, the screen of restore, registration, and deletion shown in FIG. 11B are displayed.

The designations and functions of the icons displayed in FIG. 11B are shown in FIG. 11C. As shown in FIG. 11C, a call icon calling setting, a register icon registering setting, a delete icon deleting setting, and a cancel icon canceling an operation, are displayed. In actuality, color-coded displays is used such that a selectable icon is displayed in black color, a non-selectable icon is displayed in gray color, and an icon in course of selection is displayed in yellow color.

Figure 12A:
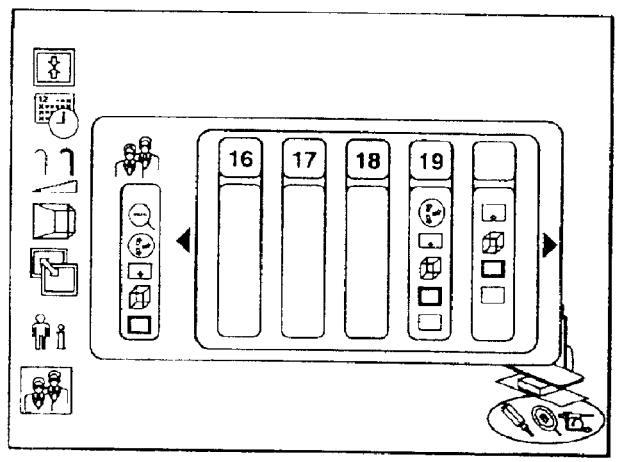
FIGS. 12A to 12C are views explaining the case where a set content such as the rotation of the scope model is called.

Next to the largest number (e.g., 19) in the registrable number range, an initial setting mark number is displayed as shown in FIG. 12A, and as this initial setting mark number, a set content that has been subjected to an initial setting is registered. When the initial setting mark number is selected, neither the register icon, nor the delete icon can be selected.

Figure 12B:
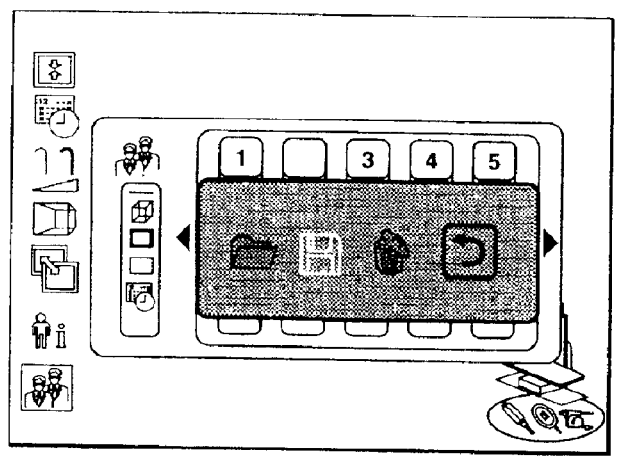

Next, the ← and/or → buttons is operated to select the register icon. Thereupon, as shown in FIG. 12B, the register icon is selected and displayed in yellow color. Then by making a determination with the ↑ or ↓ button pushed, the registration is completed.

(b) Restore

Figure 12C:
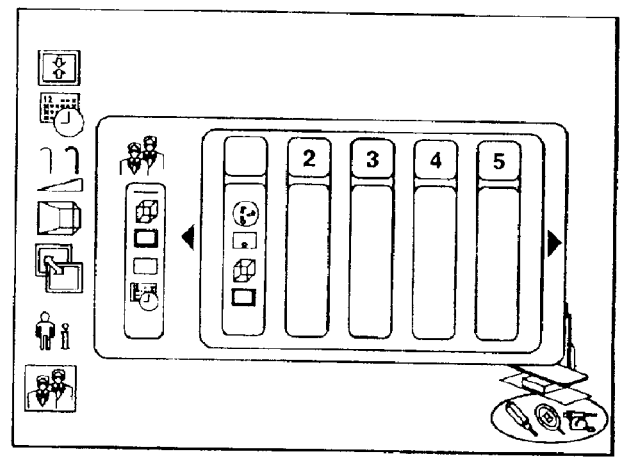
Figure 13A:
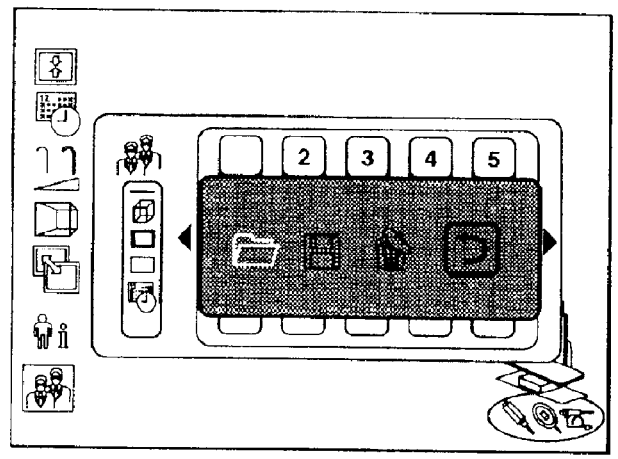
FIGS. 13A to 13C are views explaining the case where a set content such as the rotation of the scope model is deleted.

First, as in the case shown in FIG. 11A, the registration of screen setting, and the call menu shown in FIG. 12C are brought into a display state. In this display state, the cursor is moved to a number to be called by operating the by ← and/or → buttons. Thereafter, the number to be called is determined by an operation of pushing the ↑ or ↓ button. Thereupon, the screen of call, registration, and deletion shown in FIG. 13A are displayed.

Next, the ← and/or → buttons is operated to select the call icon. Thereupon, as shown in FIG. 13A, the call icon is selected and displayed in yellow color. Then by making a determination with the ↑ or ↓ button pushed, the restore is completed.

(c) Deletion

Figure 13B:
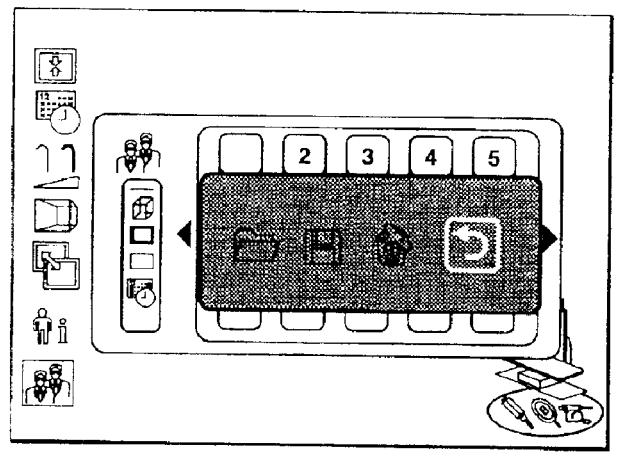

First, the registration of screen setting, and the call menu shown in FIG. 11A or 12C are brought into a display state. In this display state, the cursor is moved to a number to be deleted by operating the by ← and/or → buttons. Thereafter, the number to be deleted is determined by an operation of pushing the ↑ or ↓ button. Thereupon, the screen of call, registration, and deletion shown in FIG. 13B are displayed.

Figure 13C:
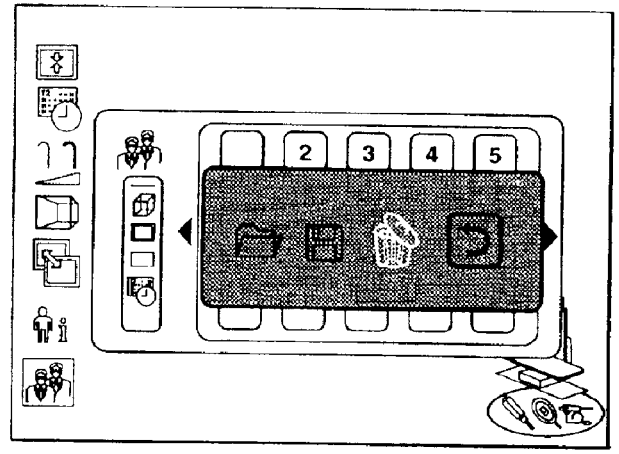

Then, the ← and/or ⊖ buttons is operated to select the delete icon. Thereupon, as shown in FIG. 13C, the delete icon is selected and displayed in yellow color. Then by making a determination with the ↑ or ↓ button pushed, the deletion is completed.

Next, the function of connection display will be described with reference to FIGS. 14A and 14B.

As described in FIGS. 1 and 4A, in this embodiment, the endoscope 6, the reference plate 58, and the extracorporeal marker 57 are detachably connected to the detecting unit 21. The presence/absence of connection is easily detected by the connection state display portion 25a of the monitor 25.

In a connected state, the connection state display portion 25a detects whether the connection state is normal, whether the endoscope 6, the reference plate 58, and the extracorporeal marker 57 are outside an effective detection range, and whether the detecting unit is abnormal or out of order, thereby allowing the user to confirm the connection state based on the display color that is displayed by changing color.

When the extracorporeal marker 57, the reference plate 58, and the endoscope 6 are detachably connected to the detecting unit 21, the extracorporeal marker connection icon, the reference plate connection icon, and the endoscope connection icon are displayed on the connection state displaying block 25a.

FIG. 14B shows the shapes and contents of the extracorporeal marker connection icon, the reference plate connection icon, and the endoscope connection icon that are displayed on the connection state displaying block 25a. The display color of the icon is arranged so as to be displayed in green color when the connection states of the extracorporeal marker 57, the reference plate 58, and the endoscope 6 are normal, in yellow color when they are outside the effective detection range, and in red color when they are damaged or out of order, thereby allowing the user to confirm the connection states thereof based on display color.

The icon is not limited to an icon that is displayed by changing the color thereof based on the determination whether the endoscope 6, the reference plate 58, and the extracorporeal marker 57 are in the effective detection range. For example, a display form wherein an icon displayed on the connection state displaying block 25a is ordinarily displayed in a non-blinking state, and wherein an icon displayed on the connection state displaying block 25a is displayed in a blinking state when the detecting unit falls out of the effective detection range, may instead be adopted.

Also, the icon is not restricted to an icon of which the display form visually displayed on the monitor 25 is changed. Alternatively, notice form that notices by sound or voice whether the detecting unit is in the effective range, may be changed. Also, with regard to the presence/absence of connection, connection state notice form is not limited to visual notice form. An form of acoustic notice by sound may instead be used. For example, when the endoscope 6, the extracorporeal marker 57, and the reference plate 58 are outside the effective detection range, a notice may be given by sound. More specifically, for example, the arrangement may be such that, when the endoscope 6, the extracorporeal marker 57, and the reference plate 58 are in the effective detection range, no sound is issued, and that, when they are outside the effective detection range, sound or voice is issued. That is, a notice may be given based on the presence/absence of sound or voice, or the change thereof.

For this purpose, as shown by double dot chain line in FIG. 4A, by connecting a voice generating device such as a speaker 99 to the CPU 32, a sound notice to the user may be given by the speaker 99 based on the determination result by the determination means 32a of the CPU 32.

In other words, when noticing the determination result as to whether the endoscope 6, the extracorporeal marker 57, and the reference plate 58 are in the effective detection range is noticed, in addition to that a notice to the user is given by changing the display form by the monitor 25 as visual display means, a notice may be given by an auditory notice form.

In this manner, in this embodiment, since the user can easily confirm whether the endoscope 6, the reference plate 58, and the extracorporeal marker 57 are in the effective detection range by viewing the display screen on the monitor, insertion operation and endoscopy can be smoothly performed. Specifically, when the endoscope 6, the reference plate 58, and the extracorporeal marker 57 are in the effective detection range, since the displayed endoscope insertion shape and the like is detected and displaced with a practicable accuracy, insertion operation and the like can be smoothly conducted. On the other hand, when the endoscope 6, the reference plate 58, and the extracorporeal marker 57 are outside the effective detection range, they can be set in the effective range, by, for example, moving the patient and the detecting unit. This allows an easy-to-use endoscope shape detector to be realized.

FIG. 15 shows the operation notice symbols of the rotations in the upward, downward, leftward, and rightward directions obtained by operating the view-angle/select button 53, a view reset obtained by pushing the reset button 52, and the state of communication with the endoscope device 2.

When the interactive communication between the detecting unit 21 and the endoscope device 2 has been established by connecting them with a communication line (e.g., RS232C), a symbol representative of a state under communication is displayed on a specified position on the display screen of the monitor 25.

FIG. 16 shows the operation notice symbols representative of the enlargement by the zoom button (+), the enlargement setting threshold value, the reduction by the zoom button (−), the reduction setting threshold value, and the viewpoint following-up.

In the display of viewpoint following-up, when the reference plate is connected to the detecting unit 21, a symbol showing that the endoscope insertion shape is displayed with the usage state of the reference plate and body-posture conversion of the patient followed up, is displayed on a specified position of the display screen.

FIG. 17 shows, as other functions, the function of a bipartite display, and a display image in the information display.

Next, more specific structure of the detecting unit 21 will be described with reference to FIGS. 18A to 20B. Here, FIGS. 18A, 18B, and 18C show a side view, a front view, and a rear elevation of the detecting unit 21, respectively.

Figure 18A:
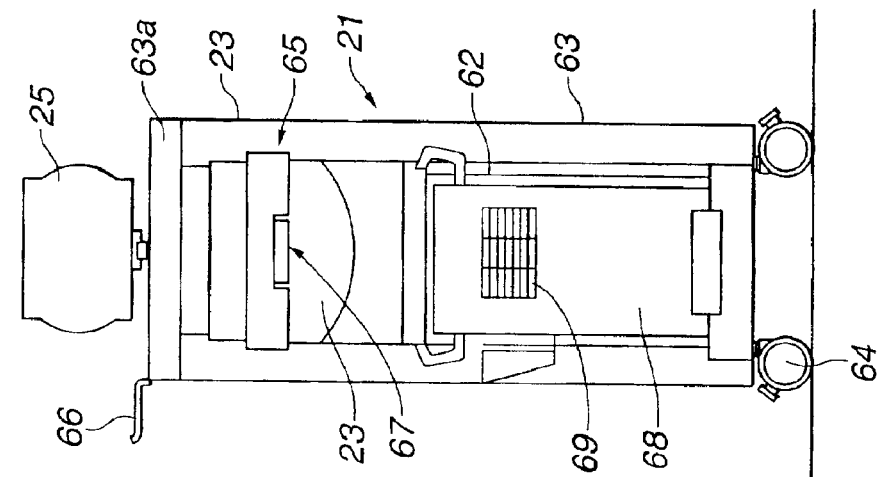
FIGS. 18A to 18C are views showing the specific shape of the detecting unit.
Figure 18B:
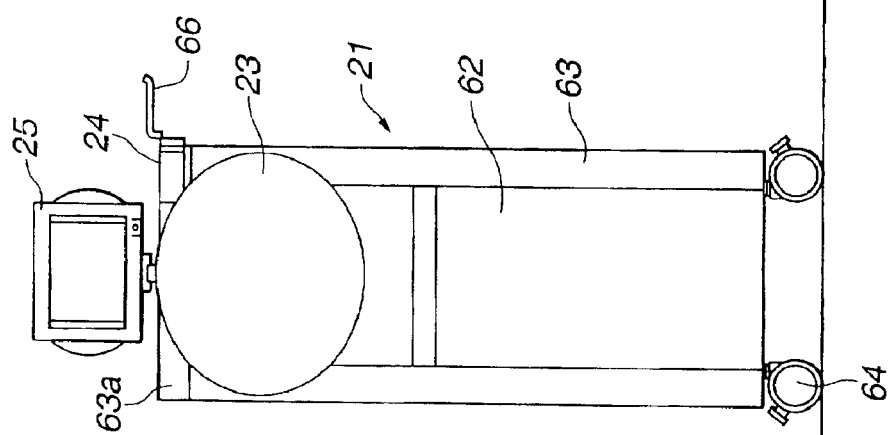
Figure 18C:
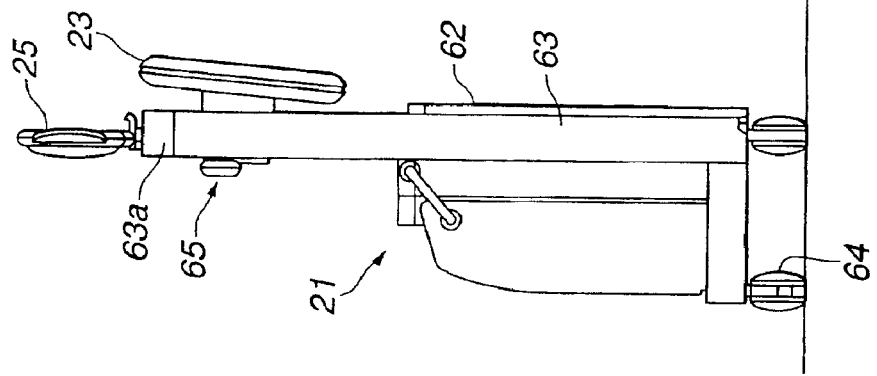

As shown in FIG. 18A and the like, the detecting unit according to the present embodiment comprises a detecting unit body 62, and a frame body 63 that holds the detecting unit body 62 so as to sandwich the bottom side and both side surfaces, a caster 64 affixed to the bottom surface of the frame body 63 so as to move the detecting unit body 62, and a crystal liquid monitor 25 disposed on the ceiling frame 63a provided on the top end of the frame body 63. Also, there is provided an operation panel 24 at a front corner portion of the ceiling frame 63a.

On the front side of the frame body 63, a disk-shaped coil unit 23 is affixed to the frame body 63 so as to be vertically moved by a hoisting and lowering mechanism 65.

On the top end of the frame body 63, there is provided a hook or a hanger 66 from which the probe 15 is hung for holding.

The detecting unit 21 is formed into an oblong form wherein the size on the side surface sides is smaller than that on the front side, and is disposed, with a small occupied area, adjacent to a side of the bed 4.

On the rear surface side of the detecting unit 21, there are provided a hoisting and lowering lever 67 constituting the hoisting and lowering mechanism 65, and an air duct 69 formed in a rear panel 68 on the rear surface of the detecting unit body 62.

Figure 19B:
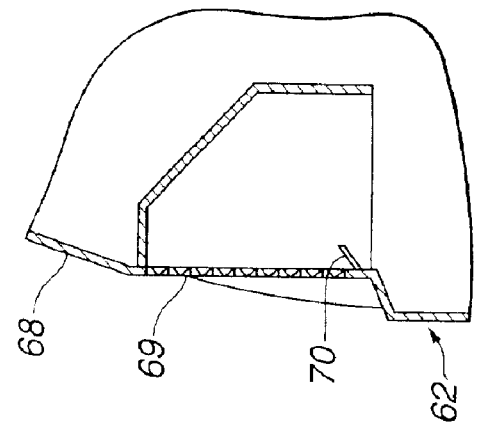
FIGS. 19A to 19C are views showing the vicinities of a duct of the detecting unit.
Figure 19C:
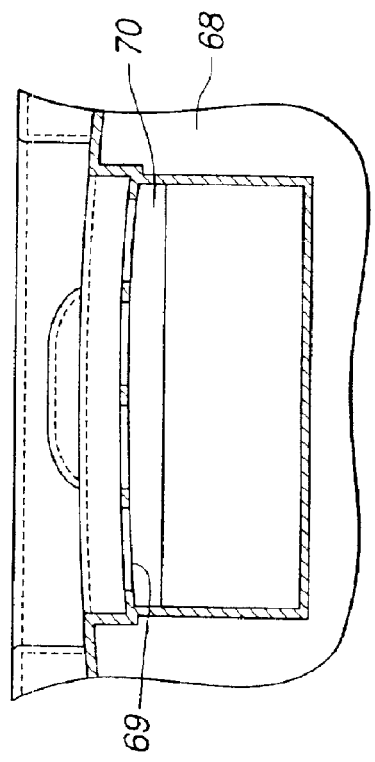
Figure 19A:
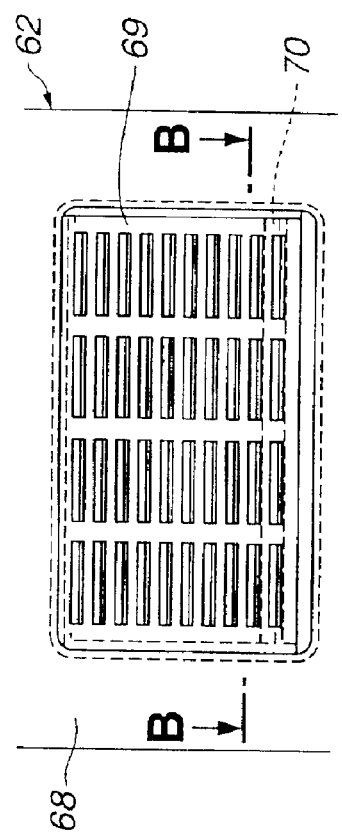

FIGS. 19A to 19C are enlarged views showing the vicinity of the air duct 69. FIG. 19A is an enlarged view seen from the rear side of the detecting unit body 62, FIG. 19B is a sectional view seen from the side thereof, and FIG. 19C is a sectional view taken along the line B—B in FIG. 19A.

As shown in FIG. 19B and others, on the inner surface of the lowermost portion of the air duct 69, a plate-shaped guide member 70 for discharging water entering the inside of the detecting unit from the duct, is disposed in an oblique direction along the horizontal direction, thereby forming a waterproof structure for the rear panel 68.

More specifically, when water and the like entering the inside of the rear panel 68 through the air duct 69 flow downward along the inside of the air duct 69, the water and the like are guided by the lower end side of the guide member 70 obliquely disposed at the lowermost portion of the air duct 69, so that the water and the like are discharged to the outside from the opening of the air duct 69, the opening facing the lower end.

Figure 20A:
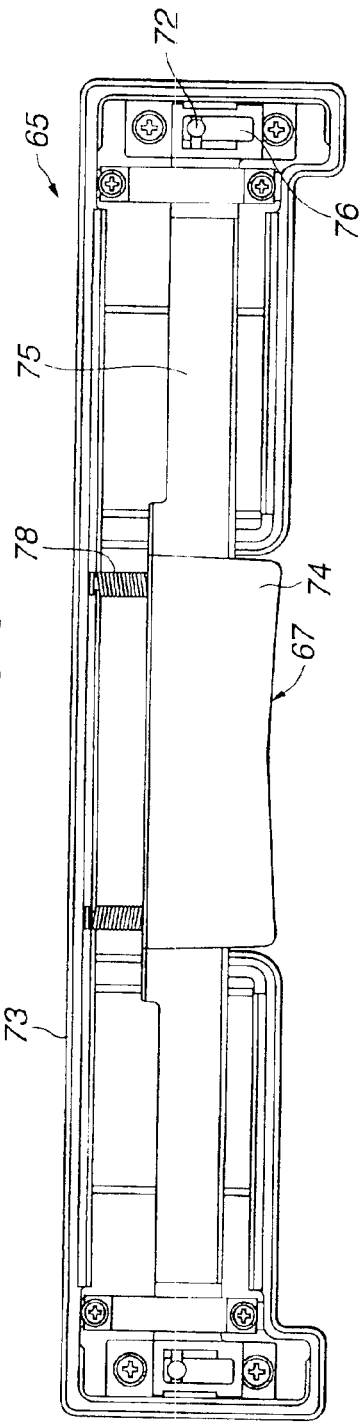
FIGS. 20A and 20B are views showing the configuration in the vicinity of a hoisting and lowering mechanism.
Figure 20B:
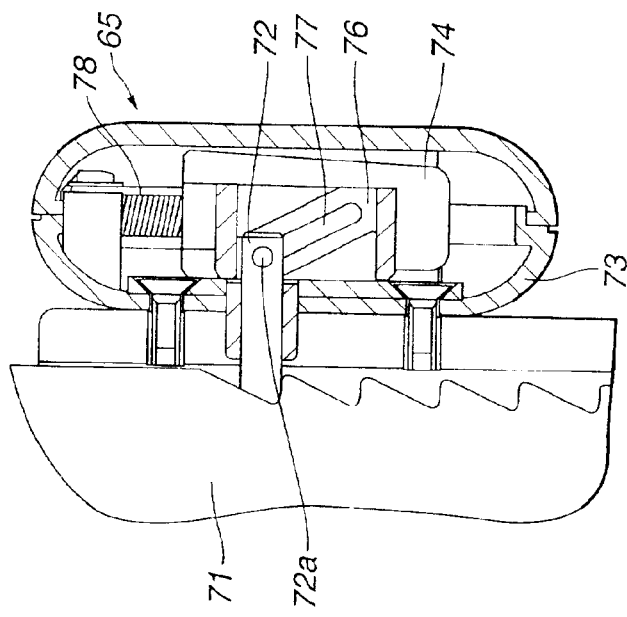

FIG. 20A shows the inner structure of the hoisting and lowering mechanism 65 wherein the base cover thereof is removed from the rear side of the detecting unit 21. FIG. 20B shows the sectional structure in the vicinity of a lock pin 72 in FIG. 20A.

The rear end side of the coil unit 23 shown in FIG. 18A and the like, is arranged so that the holding position of the coil unit 23 can be vertically movably fixed to the rack 71 (see FIG. 20B) provided in the frame body 63, by engaging the lock pins 72 with a sawtooth-shaped recesses constituting the rack 71 and vertically formed along the rack 71.

A base member 73 shown in FIG. 20A, which is long in the horizontal direction, is provided on the rear side of the coil unit 23, and a lock lever 75 integrally formed with a grip 74 is disposed inside the base member 73. In the vicinities of both ends of the lock lever 75, long grooves 76 each storing the lock pin 72, is provided. On the wall surfaces on both sides of the long groove 76, there are provided guide grooves 77 (obliquely formed) into which a guide pin 72a projected from the lock pin 72 is engaged, as shown in FIG. 20B, and the lock pin 72 is arranged so that the movement (projection and sinking) thereof is regulated by the guide grooves 77, which regulate the position of the guide pin 72a.

That is, each of the lock pins 72 is arranged so that a guide pin 72a is projectingly provided in a lateral direction, and that the guide pin 72a is engage into the guide grooves 77, thereby regulating the position of the lock pin 72.

The lock lever 75 is energized so as to be depressed by the coil spring 78. With this arrangement, when attempting to change the height position of the coil unit 23, the lock lever 75 is moved upward or downward with respect to the base member 73 with the grip 74 gripped, the guide pin 72a moves along the guide groove 77 and therewith the lock pin 72 also projects and sinks, so that the user can variably adjust the height position at which the coil unit 23 is held.

Figure 21C:
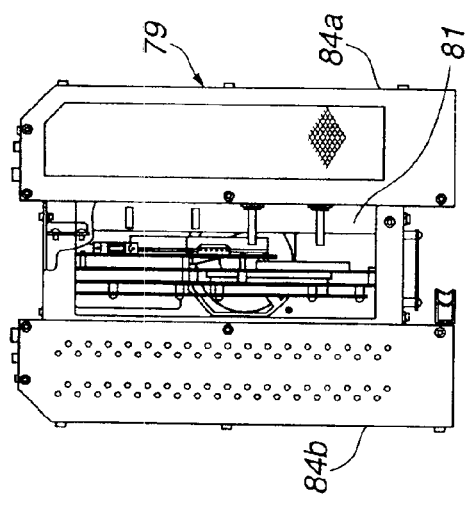
FIGS. 21A to 21C are views showing the installation configuration of transmission substrates accommodated within the detecting unit body.
Figure 21B:
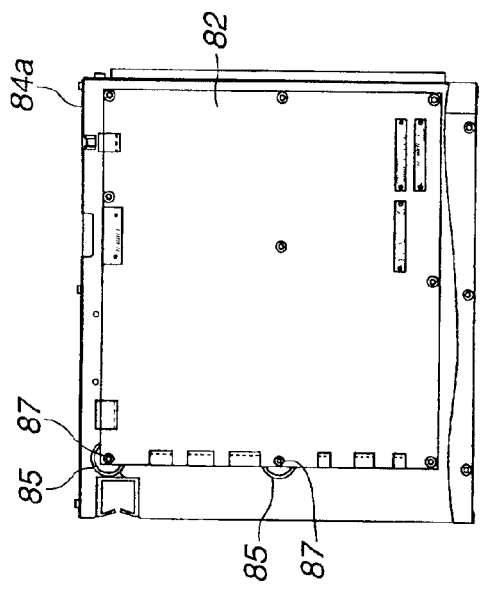
Figure 21A:
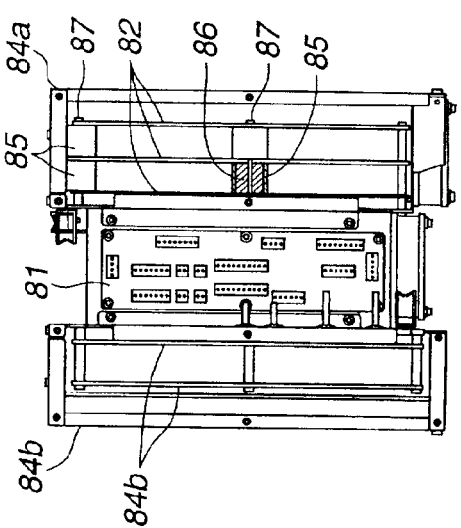

FIGS. 21A to 21C show a substrate unit 79, a control substrate 81, transmission substrates 82, and reception substrates 83, and the like within the detecting device body 62. FIG. 21A is a front view of the substrate unit 79, FIG. 21B is a side view thereof, and FIG. 21C is a top view thereof.

On the opposite sides of the control substrate 81 disposed at the center of the detecting device body 62, there are provided substrate cases 84a and 84b, respectively. The transmission substrates 82, and the reception substrates 83 are accommodated inside the substrate cases 84a and 84b, respectively.

In this case, the transmission substrates 82 constitutes a patient circuit insulated from a secondary circuit. As shown in FIG. 21A, the number of the transmission substrates 82 is, for example, three, and the plurality of transmission substrates 82 is arranged to be reliably conducted to the ground of the patient circuit, i.e., the patient ground with a small resistance, whereby the transmission substrates 82 provide a substrate installation structure capable of being installed into the substrate case 84a.

To this end, as shown in FIGS. 21A and 21B, the transmission substrate 82 is fixed to the substrate case 84a at, for example, two places, by fixing screws 87, using a hard metallic spacer 85 with a small electric resistance and an insulative spacer 86. FIG. 21A shows, in the form of a sectional view, an appearance in which a portion of transmission substrates 82 in the vicinity of the center in the longitudinal direction is fixed by the metallic spacer 85 and the insulative spacer 86.

Figure 22A:
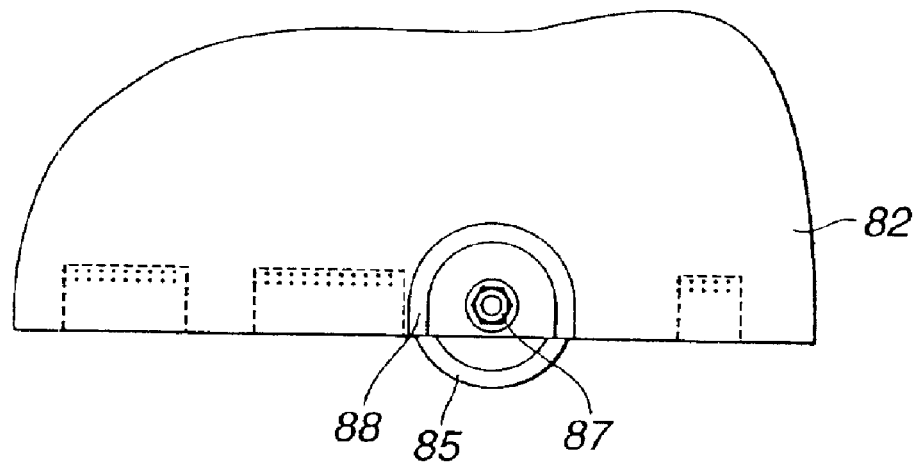
FIGS. 22A and 22B are enlarged views showing the installed portion of the transmission substrates.
Figure 22B:
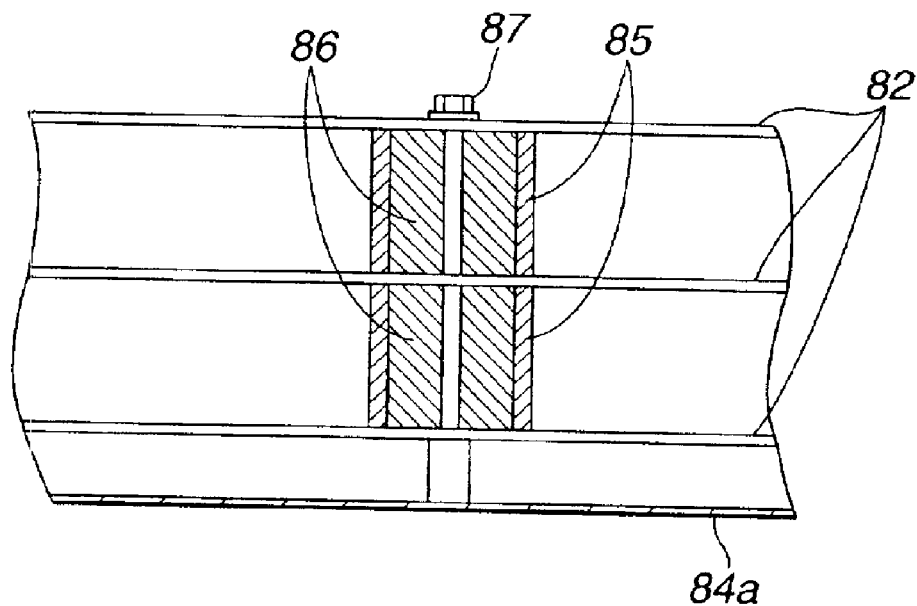

FIGS. 22A and 22B show detailed structures of the installed parts. As shown in FIG. 22B, around a hole in each of the transmission substrates 82 through which the transmission substrate 82 is fixed by the fixing screw 87, there is provided a ring-shaped ground pattern 88 concentric with the hole, as shown in FIG. 22A. However, since the ground pattern 88 is situated in the vicinity of the edge line of the transmission substrates 82, the ground pattern 88 does not take on a closed ring form such as shown in FIG. 22A.

Herein, as can be seen from FIG. 22B, the central transmission substrate 82 has GND patterns 88 formed on both surfaces thereof, and each of the transmission substrates 82 on the upper and lower sides thereof has a GND pattern formed on the surface opposite to the metallic spacer 85.

As shown in FIG. 22B, the metallic spacer 85, which is in conductive contact with the ring pattern 88, is disposed between the transmission substrates 82, and further an insulative spacer 86 constituted of an insulative material such as resin is disposed inside the metallic spacer 85, whereby the transmission substrates 82 is fixed to the substrate case 84a using a fixing screw 87 passing through the inside of the spacer 86.

In this case, the height of the insulative spacer 86 is made slightly lower than that of the metallic spacer 85 so that each of the metallic spacers 85 reliably abuts with the ring-shaped GND pattern 88, whereby the function of the patient GND can be secured. Here, the inner diameter of the GND patter 88 is determined in consideration of the power supply voltage of the substrate case 84a belonging to the secondary circuit, and the like.

Figure 24A:
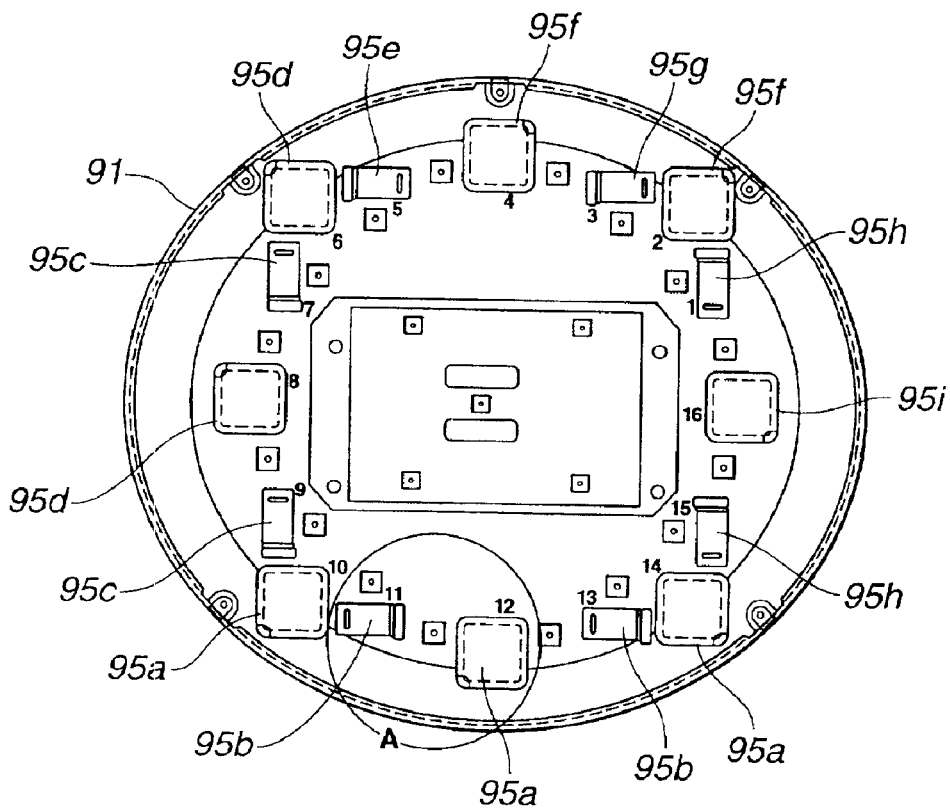
FIGS. 24A and 24B are plan views showing the configuration of the coil case and a portion thereof.
Figure 24B:
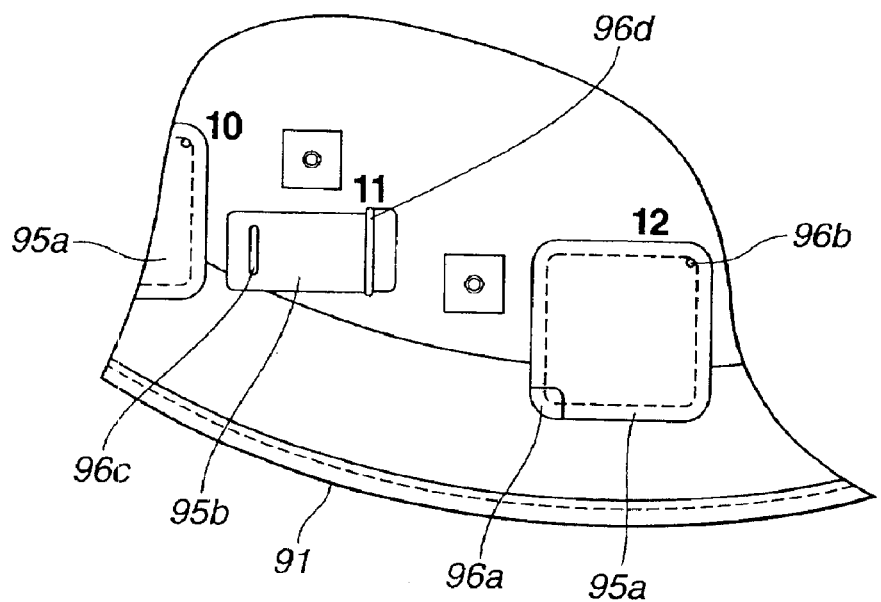

Next, descriptions will be made of the fixing mechanism of the sense coil, with reference to FIGS. 23 to 25F. FIG. 23 shows a sectional structure of a coil case 91 having sense coils fitted thereto, FIG. 24A shows the inside of the coil case 91 from which a cover is removed, and FIG. 24B is an enlarged view of a portion of the coil case 91. FIGS. 25A to 25F show each of the surfaces of the sense coils such that the shapes of the installed parts thereof to be installed into the coil case 91 are different from one another. Here, FIG. 25A is a front view of the sense coil, and FIGS. 25B and 25C are right and left side views, respectively. FIGS. 25D and 25E are top view and bottom view, respectively, and FIG. 25F is a rear elevation.

As shown in FIG. 23, to a plurality of predetermined installation positions in the coil case 91 for the coil unit 23, respective sense coils 92 are fitted, with respective predetermined installed surface provided. A retaining member 93 is placed over the coil unit 23, and by fixing the retaining member 93 to the coil case 91 by screws 94, the sense coils 92 can be easily installed into the coil case 91. Here, the sense coils 22a and 22b themselves shown in FIG. 4 and the like, plus the member covering them are designated by reference numeral 92.

More specifically, as shown in FIG. 24A, at a plurality of the predetermined installation positions in the coil case 91, there are provided recesses 95*a* to 95*i* for fitting sense coils 92 with respective predetermined fitted surfaces and respective predetermined postures provided. These recesses 95*a* to 95*i* are arranged so as to engagingly accommodate the respective corresponding surfaces in the sense coils 92, as shown in FIGS. 25A and the like.

Also, on the bottom of the recesses 95*a* to 95*i* and the like, there are provided, for example, positioning recesses 96 at a plurality of places (in FIG. 24B, specific samples of recesses 96 that are different in shape from one another are denoted by reference numerals 96*a* to 96*d*), and as shown in FIGS. 25A to 25F, these recesses 96 are arranged so as to engagingly accommodate projections 97 provided on respective corresponding surfaces. Here, the projections 97 shown in FIGS. 25C and 25F are denoted by specific reference numerals 97*a*, 97*b*, 97*c*, and 97*d* for the sake of facilitating the understanding the descriptions below.

In FIG. 24A, in order for sixteen sense coils 92 to be unerringly installed, numbers 1 to 16 are assigned to them. FIG. 24B is an enlarged view of the portion indicated by the circle A FIG. 24A.

In FIG. 24A, for example, the recesses 95*a* and 95*d* are mutually different in the positions where the recesses 96 are disposed, and therefore, the sense coils 92 are installed into the recesses 95*a* and 95*d* in a state wherein the orientations of the installed surfaces thereof are different from each other.

For example, in the recesses 95*a* in FIG. 24B, the surface shown in FIG. 25F is arranged so that projections 97*a* and 97*b* in FIG. 25F is engaged in recesses 96*a* and 96*b* in FIG. 26B, respectively. Also, the surface in FIG. 25C is engaged in recess 95*b* in FIG. 24B, and projections 97*c* and 97*d* are engaged into recesses 96*c* and 96*d* in FIG. 24B, respectively.

In this manner, the sense coils 92 are arranged so as to be fitted to respective corresponding installation positions with ease and high accuracy. Additionally, the sense coil 92 includes recesses 98.

Meanwhile, the sense coils 92 are also provided with recesses 98.

Thus, when a plurality of sense coils 92 used for magnetic-field detection is to be fitted to respective corresponding predetermined positions of the coil case 91, each of the surfaces of the plurality of sense coils is provided with the projections 97 that are different in size and shape from those on other surface, and these projections are engaged into the recesses 95*a* to 95*i* provided on the coil case 91 side, whereby a structure that defines the installed surfaces and orientations of the sense coils 92 is achieved, so that the sense coils can be fitted to respective corresponding positions thereof including orientations thereof with accuracy and unerringness. In addition, these sense coils 92 are arranged to be capable of accurately detecting the endoscope shape.

It is obvious from the above descriptions that the projections may be disposed on the sense coil 92 side and that the recesses may be disposed on the coil case 91 side. Also, although the sense coils 92 are installed into the coil case 91, the sense coils 92 may be arranged to be installed on a substrate and accommodated in the coil case 91.

In the above descriptions, it has been explained that the coils on the sides of the probe 15, the extracorporeal marker 57, and the reference plate 58 are source coils generating magnetic fields and that the coils on the coil unit 23 side are sense coils. However, the above-described relationship may be inverted. In other words, the arrangement may be such that the coils on the sides of the probe 15, the extracorporeal marker 57, and the reference plate 58 are sense coils detecting magnetic fields and that the coils on the coil unit 23 side are source coils generating the magnetic fields.

As evident from the foregoing, according to the present embodiment, the insertion shape of the endoscope inserted portion or the display form in the position display of the other equipment can be selectively displayed by the display means, based on the outputs of the detecting means, and therefore, if the endoscope and/or the other equipment fall out of the shape detection range, the operator can easily notice it.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope shape detector for detecting an endoscope shape, the detector comprising:
   a device to be detected, the device being disposed in an endoscope inserted portion adapted to be inserted into a subject, or in other equipment;
   a detecting unit that detects the position of the device to be detected;
   a display device that displays the insertion shape of the endoscope inserted portion or the position of the other equipment, on the basis of position information detected by the detecting unit;
   a determining device that determines whether the device to be detected is in an effective detection range of the detecting unit, on the basis of the output of the detecting unit; and
   a display form selecting device that selects a display form by the display device, in the insertion shape display of the endoscope inserted portion, or a display form by the display means, in the position display of the other equipment, on the basis of the determination result of the determining device.

2. An endoscope shape detector according to claim 1, wherein the display form selecting device selects a display color depending on whether the endoscope inserted portion or the other equipment is in the effective detection range, whereby the display form selecting device displays it.

3. An endoscope shape detector according to claim 1, wherein the display form selecting device performs a display in a blinking form or in a non-blinking form, depending on whether the endoscope inserted portion or the other equipment is in the effective detection range.

4. An endoscope shape detector according to claim 1, wherein the display form selecting device changes a sound content, the presence/absence of a sound notice, or a notice form by a change in sound, depending on whether the endoscope inserted portion or the other equipment is in the effective detection range.

5. An endoscope shape detector for detecting an endoscope shape, the detector comprising:
   a detecting unit that detects the position of the device to be detected;
   a display device that displays the position of the device to be detected, on the basis of the output of the detecting unit;
   a determining device that determines whether the device to be detected is in an effective detection range of the detecting unit, on the basis of the output of the detecting unit; and a display form noticing device that notices display forms of endoscope peripheral equipment including an endoscope having the device to be detected therein, on the basis of the determination result of the determining device.

6. An endoscope shape detector according to claim 5, wherein the display form noticing device selects a display color to display, by the display device, the device to be detected or the endoscope peripheral equipment, depending on whether the device to be detected is in the effective detection range, whereby the display form noticing device displays it.

7. An endoscope shape detector according to claim 5, wherein the display form noticing device performs a display in a blinking or a non-blinking form when displaying, on the display device, the device to be detected or the endoscope peripheral equipment, depending on whether the device to be detected is in the effective detection range.

8. An endoscope shape detector according to claim 5, wherein the display form noticing device changes a sound content, the presence/absence of a sound notice, or a notice form by a change in sound, depending on whether the endoscope peripheral equipment is in the effective detection range.

9. An endoscope shape detector according to claim 5, wherein the endoscope peripheral equipment, which the display form noticing device notices, is endoscope supplemental equipment used for supplementing an endoscope insertable portion of the endoscope.

10. An endoscope shape detector according to claim 5, wherein the device to be detected is a coil that generates or detects a magnetic field.

11. An endoscope shape detector according to claim 5, wherein the endoscope peripheral equipment, which the display form noticing device notices, has a connector detachable with respect to the detecting unit, and wherein the detecting unit has a connection detecting device that performs connection detection as to whether the connector has been connected to the detecting unit.

12. An endoscope shape detector according to claim 11, wherein information corresponding to the detection result of connection/non-connection by the connection detecting device is displayed on the display device.

13. An endoscope shape detector according to claim 12, wherein the information is arranged so that, in the case of connection detection, a model corresponding to the endoscope peripheral equipment is displayed on the display device, and that, in the case of non-connection detection, no display is performed.

14. An endoscope shape detector for detecting an endoscope shape, the detector comprising:
a device to be detected, the device being disposed either in an endoscope inserted portion inserted into a subject or outside the subject;
a sensing unit that detects information from the device to be detected, disposed either in the endoscope inserted portion or outside the subject;
a detecting device to which the device to be detected and the sensing unit are connected, having a CPU for calculating the insertion shape of the endoscope inserted portion or the position of the device to be detected based on the information of the position of the device to be detected as detected by the sensing unit;
a connection detecting device that detects whether the device to be detected or the sensing unit has been connected to the detecting device;
a connection state display portion that displays the result of detection of the connection detecting device,
wherein the device to be detected or the sensing unit includes an extra corporeal marker for showing the extra corporeal position thereof and of the device disposed in the endoscope inserted portion;
a determining device that determines whether the device to be detected is in the effective detection range of the detecting unit, on the basis of the output of the detecting unit; and
a display form selecting device that selects a display form in a insertion shape display of the endoscope inserted portion or a display form in a position display of the device to be detected, on the basis of the determination result of the determining device.

15. An endoscope shape detector for detecting an endoscope shape, the detector comprising:
a device to be detected, the device being disposed in an endoscope inserted portion adapted to be inserted into a subject, or in other equipment;
a detecting unit that detects the position of the device to be detected; and
a display device that displays the insertion shape of the endoscope inserted portion or the position of other equipment, on the basis of position information detected by the detecting unit,
wherein the detecting unit comprises a plurality of coils for magnetic-field detection or magnetic-field generation, and installation substrates on which the plurality of coils is fitted to respective predetermined positions, wherein each surface of the plurality of coils is provided with a projection that is different in size and shape from the projections of other surfaces, and wherein an installed surface and the orientation of each of the coils are defined by engaging the projection thereof with a respective corresponding recess provided on the coil.

16. An endoscope shape detector for detecting an endoscope shape, the detector comprising:
a device to be detected, the device being disposed in an endoscope inserted portion adapted to be inserted into a subject, or in other equipment;
a detecting unit that detects the position of the device to be detected;
a display device that displays the insertion shape of the endoscope inserted portion or the position of other equipment, on the basis of position information detected by the detecting unit;
a determining device that determines whether the device to be detected is in the effective detection range of the detecting unit, on the basis of the output of the detecting unit; and
a notice form selecting device that selects a visual notice form in the insertion shape display of the endoscope inserted portion or the position display of the other equipment on the basis of the determination result of the determining device, or an acoustic notice form using sound or voice on the basis of the determination result.

17. An endoscope shape detector for detecting an endoscope shape, the detector comprising:
a device to be detected, the device being disposed in an endoscope inserted portion adapted to be inserted into a subject, or in other equipment;
a detecting unit that detects the position of the device to be detected; and
a display device that displays the insertion shape of the endoscope insertable portion or the position of other equipment, on the basis of position information detected by the detecting unit, wherein the detecting unit is arranged so that the holding position thereof is vertically movable along a rack vertically provided, and wherein the detecting unit includes a lock lever integrally formed with a grip, which is gripped when ascent and descent operations are performed, tilted grooves provided at both ends of the lock lever, and pins movable along the grooves.

18. An endoscope shape detector according to claim 17, wherein the detecting unit has a substrate case, and wherein, when a plurality of substrates each constituting a patient circuit insulated from a second circuit is fixed to the substrate case, all of the substrates are stacked with an insulative spacer interposed therebetween and fixed to the substrate case with a screw passing through the insulative spacer; the outside of the insulative spacer is covered with a hard electrically conductive spacer; the height of the hard conductive spacer is made slightly higher than that of the insulative spacer; and a conductive pattern that conducts to the ground of the patient circuit, is formed at the portion in each of the substrates against which the end portion of the hard conductive spacer abuts.

19. An endoscope shape detector according to claim 17, wherein the detecting unit has an air duct, and wherein a guide member for discharging water entering the inside of the detecting unit from the duct, is disposed in an oblique direction on the inner surface of the lowermost portion of the duct.

* * * * *